United States Patent [19]

Sawada et al.

[11] 4,393,228

[45] Jul. 12, 1983

[54] EPOXYSUCCINIC ACID DERIVATIVES

[75] Inventors: Jiro Sawada, Kodaira; Kazunori Hanada; Masaharu Tamai, both of Ageo; Shigeo Morimoto, Saitama; Sadafumi Omura, Ageo, all of Japan

[73] Assignee: Taisho Pharmaceutical Co., Ltd., Tokyo, Japan

[21] Appl. No.: 880,180

[22] Filed: Feb. 22, 1978

[30] Foreign Application Priority Data

Mar. 3, 1977 [JP] Japan .................................. 52-23092
Mar. 4, 1977 [JP] Japan .................................. 52-23536
Mar. 4, 1977 [JP] Japan .................................. 52-23537

[51] Int. Cl.$^3$ ................. C07D 303/48; C07D 407/12; C07D 411/12; C07D 407/02
[52] U.S. Cl. .................................... 549/549; 542/427; 548/336; 548/372; 549/60; 549/435; 549/473
[58] Field of Search .................... 260/348.62, 348.46; 542/427; 549/549, 473, 60, 435; 548/372, 336

[56] References Cited

U.S. PATENT DOCUMENTS 3,911,111 10/1975 Sawada et al. ...................... 424/118
4,064,241 12/1977 Ross ..................................... 424/246

FOREIGN PATENT DOCUMENTS 52-19652 2/1977 Japan .

OTHER PUBLICATIONS

K. Hanada et al., Agric. Biol. Chem., vol. 42(3) (1978), pp. 523–536.
Edward B. Roche, Design of Biopharmaceutical Properties through Prodrugs and Analogs (American Pharmaceutical Assoc.), (1977), pp. 346–347.

*Primary Examiner*—Norma S. Milestone
*Attorney, Agent, or Firm*—Kenway & Jenney

[57] ABSTRACT

The epoxysuccinic acid derivatives of this invention are prepared by esterification of an epoxysuccinic acid or a halide thereof, by partial hydrolysis of an epoxysuccinic acid diester, by amidation of an epoxysuccinic acid monoester, or by hydrolysis of an epoxysuccinic acid amide monoester. These epoxysuccinic acid derivatives have excellent thiol protease inhibitory activity and anti-inflammatory activity without the acceleration of vascular permeability.

14 Claims, No Drawings

EPOXYSUCCINIC ACID DERIVATIVES

BACKGROUND

Prior to the present invention, E-64 has been the only known epoxysuccinic acid compound possessing thiol protease inhibitory activity together with anti-inflammatory activity as described in U.S. Pat. No. 3,911,111. This compound, however, has an undesirable side effect, i.e., the acceleration of vascular permeability.

The novel epoxysuccinic acid derivatives of the present invention are distinguished from the prior art patented compound by their excellent thiol protease inhibitory activity and anti-inflammatory activity and by the absence of the acceleration of vascular permeability as shown in tests upon laboratory animals.

DESCRIPTION AND PREFERRED EMBODIMENTS

This invention relates to a novel trans epoxysuccinic acid derivative represented by the general formula

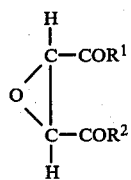
(I)

wherein (1) $R^1$ and $R^2$ are each $R^3$ wherein $R^3$ is $-O-A^1-R^4$, $-O-A^2-R^5$ or $-OCH_2-R^6$ wherein $A^1$ is alkylene containing zero to 4 carbon atoms or said alkylene substituted with methyl, $R^4$ is cycloalkyl containing 3 to 10 carbon atoms, or said cycloalkyl substituted with one to 3 halogen or methyl, $A^2$ is alkylene containing 2 or 3 carbon atoms or alkenylene containing 2 or 3 carbon atoms, $R^5$ is phenyl, $R^6$ is furyl, tetrahydrofuryl, thienyl, naphthyl, naphthyl substituted with one or two halogens or methyl, or phenyl substituted with one to three halogen, methyl, methoxy, methylenedioxy or trifluoromethyl groups, or cycloalkenyl containing 5 to 8 carbon atoms, or (2) $R^1$ is hydroxy, $R^3$ or $R^7$, and $R^2$ is hydroxy or $R^8$ wherein $R^3$ is as defined above, $R^7$ is alkoxy containing one to 12 carbon atoms, allyloxy, propargyloxy, phenoxy or benzyloxy, and $R^8$ is an amino acid residue represented by the general formula

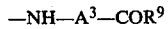

wherein $A^3$ is methylene, ethylene, trimethylene, alkylidene containing 2 to 5 carbon atoms or said alkylidene substituted with one to 3 hydroxy, methyl, thiol, methylthio, benzylthio, phenyl, phenyl substituted with hydroxy or halogen, indazolyl, imidazolyl, $-COR^{10}$ or $-NHR^{11}$ wherein $R^{10}$ is amino or $-OR^{12}$ wherein $R^{12}$ is hydrogen, alkyl containing one to 5 carbon atoms, benzyl or an alkali metal cation, and $R^{11}$ is hydrogen, formyl, alkoxycarbonyl containing 2 to 5 carbon atoms, benzyloxycarbonyl, methoxybenzyloxycarbonyl, tosyl, guanyl, or guanyl substituted by nitro, and $R^9$ is amino or $-OR^{13}$ is hydrogen, alkyl containing one to 5 carbon atoms, benzyl or an alkali metal cation with the proviso that $R^1$ is neither hydroxy, alkoxy containing one to 12 carbon atoms, nor phenoxy when $R^2$ is hydroxy, and salts thereof when $R^1$ or $R^2$ is hydroxy.

In this specification and claims, unless otherwise noted, the term "halogen" or "halo" refers to chloro, bromo, iodo and fluoro, and the epoxysuccinic acid derivatives are limited to the trans isomers, namely, the two carbonyl groups on the oxirane ring are in trans configuration each other.

With regard to the compound of this invention, examples of $-O-A^1-R^4$ are $-O-R^4$, $-OCH_2-R^4$, $-O-(CH_2)_2-R^4$, $-O-(CH_2)_3-R^4$, and $-O-(CH_2)_4-R^4$. Examples of the alkylene substituted with methyl in $A^1$ are methylmethylene, 1- or 2-methylethylene, 1-, 2- or 3-methylpropylene, or 1-, 2-, 3- or 4-methylbutylene. Examples of the cycloalkyl containing 3 to 10 carbon atoms in $R^4$ are cyclopropyl, cyclobutyl, cyclopentyl, cyclohexyl, cycloheptyl, bicycloheptyl, cyclooctyl, bicyclooctyl, adamantyl, and the like. The substituent on the cycloalkyl in $R^4$ may be on any position, and when 2 or 3 substituents are present, they are the same or different. Examples of the cycloalkenyl in $R^6$ are cyclopentenyl, cyclohexenyl, bicycloheptenyl, cyclooctenyl and the like. Examples of $-O-A^2-R^5$ are 2-phenylethyloxy, 3-phenylpropyloxy, cinnamyloxy, styryloxy and the like. Each substituent on naphthyl and phenyl in $R^6$ may independently be on any position, and when 2 or 3 substituents are present, they may be the same or different. Examples of the alkoxy containing one to 12 carbon atoms in $R^7$ are methoxy, ethoxy, propoxy, butoxy, pentyloxy, hexyloxy, heptyloxy, octyloxy, nonyloxy, decyloxy, undecyloxy, dodecyloxy and isomeric forms thereof.

The substituent on the alkylidene in $A^3$ may be on any position, and when 2 or 3 substituents are present, they are the same or different. The substituent on phenyl attached to the alkylidene in $A^3$ may be on any position, and when two or three substituents are present, they may be the same or different. Examples of the alkali metal cations in $R^{12}$ or $R^{13}$ are independently potassium or sodium. Examples of the amino acid corresponding to said amino acid residue are glycine, α- or β-alanine, valine, leucine, serine, threonine, methionine, phenylalanine, tyrosine, cysteine, asparagine, glutamine, histidine, tryptophan, aspartic acid, lysine, glutamic acid, hydroxylysine, arginine, ornithine, γ-amino butylic acid and the like, and those with a suitable protective group.

The salts of the compound(I) wherein $R^1$ or $R^2$ is hydroxy, are those with alkali metal cations such as potassium and sodium.

In a preferred embodiment of this invention, epoxysuccinic acid derivatives of this invention may be prepared by the following reaction sequence.

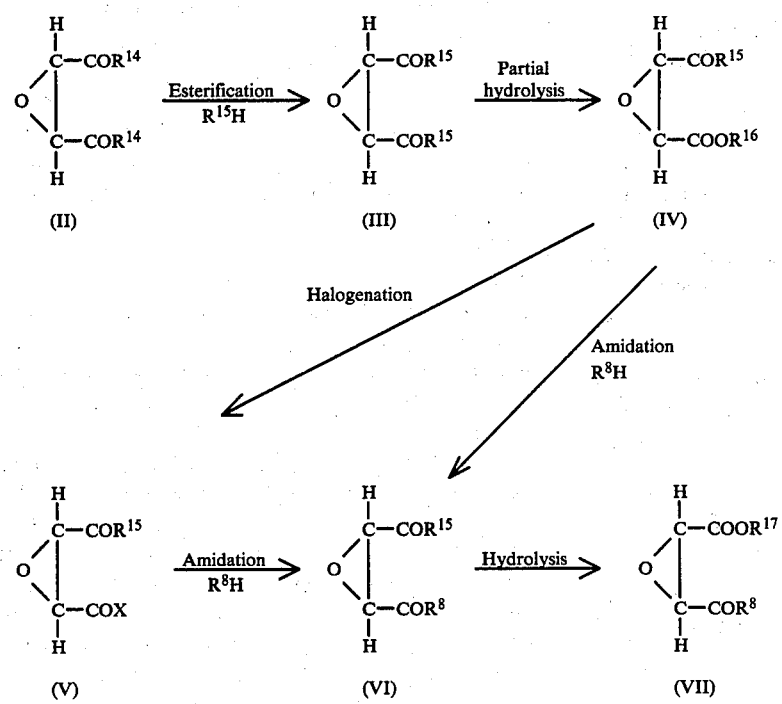

(II)　　　　　　　　(III)　　　　　　　(IV)

(V)　　　　　　　　(VI)　　　　　　　(VII)

In this reaction sequence, $R^{14}$ is hydroxy or halogen, $R^{15}$ is $R^3$ or $R^7$, $R^{16}$ and $R^{17}$ are independently hydrogen or alkali metal cation, X is halogen, and $R^8$ is as defined above. The starting material(II) wherein $R^{14}$ is halogen may be dissolved in an organic solvent such as ethyl ether, benzene and cyclohexane. To the resulting solution, $R^{15}H$ may be added along with an organic base such as triethylamine, pyridine and methylmorphorine to give the epoxysuccinic acid diester(III). Also, to the starting material(II) wherein $R^{14}$ is hydroxy in the same organic solvent as described above, $R^{15}H$ may be added in the presence of an acid catalyst such as sulfuric acid to give the epoxysuccinic acid diester(III).

The epoxysuccinic acid diester(III) thus obtained may be dissolved in an organic solvent or a mixture of the organic solvent and water. Examples of said organic solvent are dioxane, acetone, tetrahydrofuran, dimethylformamide, dimethylsulfoxide, and alcohols such as ethanol, methanol and $R^{15}H$. To the resulting solution, a caustic alkali such as potassium hydroxide, sodium hydroxide or the like in the same solvent as described above or water may be added with ice-cooling or at room temperature. Equimolecular quantities of the caustic alkali have to be used in this reaction. The resulting mixture may be stirred for 5 to 120 minutes, and then, if necessary, followed by addition of acetone, dioxane, ethyl ether or petroleum ether to give the compound(IV) wherein $R^{16}$ is an alkali metal cation. The compound(IV) wherein $R^{16}$ is alkali metal cation may be acidified with an inorganic acid such as sulfuric acid, hydrochloric acid and the like, and extracted with an organic solvent such as ethyl acetate or benzene to give the compound(IV) wherein $R^{16}$ is hydrogen.

The compound(IV) wherein $R^{16}$ is hydrogen or alkali metal cation may be dissolved in an organic solvent such as ethyl ether, benzene, cyclohexane, dimethylformamide, dichloromethane and the like, and then treated with a halogenating agent such as oxalyl chloride to give the compound(V). The compound(V) thus obtained, may be dissolved in an organic solvent such as benzene, ethyl ether or dichloromethane together with an organic base such as triethylamine, pyridine, methylmorphorine or the like with ice-cooling or room temperature to give the compound(VI).

In another method, the compound(IV) wherein $R^{16}$ is hydrogen may be dissolved in an organic solvent such as ethyl ether, benzene, cyclohexane, dimethylformamide, dichloromethane, tetrahydrofuran and the like, and then reacted with $R^8H$ in the presence of a condensing agent such as dicyclohexylcarbodiimide and/or in the presence of hydroxysuccinoimide or 1-hydroxybenzotiazole to give the compound(VI).

The compound(VI) thus obtained may be dissolved in water, an organic solvent such as ethanol, benzylalcohol, dioxane, ethyl ether and the like, or in a mixture of water and the organic solvent. The resulting solution may be reacted with the equimolar of a caustic alkali such as potassium hydroxide, sodium hydroxide and the like in the same solvent as described above with ice-cooling or at room temperature. The resulting mixture may be stirred for 5 to 120 minutes, and then, if necessary, followed by addition of ethanol, acetone, dioxane, ethyl ether or petroleum ether to give the alkali metal salt of the compound(VII). If desired, the protecting groups attached to carbonyl in $R^8$ of the compounds(VI) or (VII) may be removed by the addition of an excess amount of said caustic alkali.

The alkali metal salt obtained may be collected by filtration, and purified by washing or recrystallization. The salt may be acidified with an inorganic acid such as sulfuric acid, and extracted with an organic solvent such as ethyl acetate or benzene to give the free acid.

If desired, the protecting groups attached to amino or carboxyl in $R^8$ of the compound(VI) or (VII) may be removed by catalytic reduction using palladium carbon or palladium black.

The starting material(II) wherein $R^{14}$ is hydroxy can be prepared by the method as described in Journal of Organic Chemistry, 24, 54(1959), and the starting material(II) wherein $R^{14}$ is halogen can be prepared by the method as described in Journal of Medical Chemistry, 6, 233(1963), or by that with some modification. Furthermore, $R^3H$, $R^7H$ and $R^8H$ are to a large extent commercially available.

The compounds of this invention inhibit effectively and specifically thiol proteases such as papain, bromelains and some kinds of cathepsin in which some sulfhydryl groups are essential for activity. On the other hand, the compounds of this invention, have no inhibitory activity against proteolysis of casein by trypsin, chymotrypsin, pepsin, acid protease of Peacilomyces varioti or Nagarse (trademark of Nagase Industry), esterolysis of benzoylarginine ethyl ester by kallikrein, or against fibrinolysis by human plasmin.

Papain inhibitory activity of the compounds of this invention was assayed as follows: To 0.5 ml of a solution of papain (80 μg/ml, Sigma Chem. Co., 2x cry.), were added 0.25 ml of 40 mM cysteine dissolved in 20 mM disodium ethylenediamine tetraacetic acid solution adjusted pH to 6.8 with sodium hydroxide and 0.25 ml of 33 mM phosphate buffer (pH 6.8) with or without inhibitor. After incubation at 40° C. for 15 minutes, the resulting mixture was added to 5 ml of 1% milk casein solution in the same buffer as described above, and further incubated at 40° C. for 10 minutes. Then the mixture was mixed with 5 ml of 0.44 M trichloroacetic acid solution and followed by filtration with a sheet of Toyo filter paper No. 4. The extinction of the filtrate was read at 280 nm. The percent inhibition was calculated from the formula, 100 x (B-A)/B; wherein B stands for the absorbance without inhibitor and A for the absorbance with inhibitor. The amount of inhibitor for 50% inhibition was expressed as $ID_{50}$, and shown in Table 1. The compound Nos. in Table 1 are as defined in Examples as described hereinafter.

TABLE 1

| Compound No. | $ID_{50}(\gamma)$ | Compound No. | $ID_{50}(\gamma)$ | Compound No. | $ID_{50}(\gamma)$ |
|---|---|---|---|---|---|
| EP - 1 | 1.98 | EP - 35 | 0.98 | EP - 69 | 0.23 |
| - 2 | 0.07 | - 36 | 0.07 | - 70 | 0.08 |
| - 3 | 2.12 | - 37 | 0.22 | - 71 | 0.40 |
| - 4 | 0.09 | - 38 | 0.06 | - 72 | 0.08 |
| - 5 | 2.36 | - 39 | 4.39 | - 73 | 0.10 |
| - 6 | 0.09 | - 40 | 0.34 | - 74 | 0.07 |
| - 7 | 2.25 | - 41 | 0.27 | - 75 | 1.65 |
| - 8 | 0.07 | - 42 | 0.06 | - 76 | 0.82 |
| - 9 | 2.20 | - 43 | 0.45 | - 77 | 0.77 |
| - 10 | 0.06 | - 44 | 0.07 | - 78 | 0.54 |
| - 11 | 2.50 | - 45 | 0.23 | - 79 | 0.75 |
| - 12 | 0.07 | - 46 | 0.08 | - 80 | 0.32 |
| - 13 | 2.50 | - 47 | 0.25 | - 81 | 1.30 |
| - 14 | 0.10 | - 48 | 0.08 | - 82 | 0.34 |
| - 15 | 1.69 | - 49 | 0.85 | - 83 | 1.55 |
| - 16 | 0.08 | - 50 | 0.09 | - 84 | 0.29 |
| - 17 | 1.79 | - 51 | 0.30 | - 85 | 1.56 |
| - 18 | 0.08 | - 52 | 0.07 | - 86 | 0.27 |
| - 19 | 2.01 | - 53 | 0.45 | - 87 | 1.58 |
| - 20 | 0.06 | - 54 | 0.09 | - 88 | 0.32 |
| - 21 | 2.46 | - 55 | 0.28 | - 89 | 1.39 |
| - 22 | 0.12 | - 56 | 0.06 | - 90 | 0.25 |
| - 23 | 2.45 | - 57 | 0.26 | - 91 | 0.35 |
| - 24 | 0.09 | - 58 | 0.07 | - 92 | 0.10 |
| - 25 | 3.03 | - 59 | 0.18 | - 93 | 4.31 |
| - 26 | 0.08 | - 60 | 0.10 | - 94 | 0.27 |
| - 27 | 20.00 | - 61 | 1.18 | - 95 | 4.20 |
| - 28 | 0.80 | - 62 | 0.08 | - 96 | 0.37 |
| - 29 | 3.12 | - 63 | 54.82 | - 97 | 3.20 |
| - 30 | 0.07 | - 64 | 0.10 | - 98 | 0.32 |
| - 31 | 3.25 | - 65 | 69.44 | - 99 | 0.50 |
| - 32 | 0.09 | - 66 | 0.08 | - 100 | 0.10 |

TABLE 1-continued

| Compound No. | $ID_{50}(\gamma)$ | Compound No. | $ID_{50}(\gamma)$ | Compound No. | $ID_{50}(\gamma)$ |
|---|---|---|---|---|---|
| - 33 | 3.20 | - 67 | 93.28 | - 101 | 1.51 |
| - 34 | 0.07 | - 68 | 0.10 | - 102 | 0.36 |
| - 103 | 1.06 | - 137 | 2.08 | - 171 | 5.80 |
| - 104 | 0.36 | - 138 | 0.82 | - 172 | 6.20 |
| - 105 | 0.40 | - 139 | 0.78 | - 173 | 5.80 |
| - 106 | 0.14 | - 140 | 0.92 | - 174 | 0.20 |
| - 107 | 0.15 | - 141 | 1.45 | - 175 | 1.90 |
| - 108 | 0.09 | - 142 | 0.29 | - 176 | 1.06 |
| - 109 | 0.50 | - 143 | 0.15 | - 177 | 1.50 |
| - 110 | 0.24 | - 144 | 0.34 | - 178 | 4.63 |
| - 111 | 2.91 | - 145 | 0.14 | - 179 | 1.60 |
| - 112 | 0.32 | - 146 | 0.39 | - 180 | 9.76 |
| - 113 | 0.99 | - 147 | 3.40 | - 181 | 6.59 |
| - 114 | 0.26 | - 148 | 0.70 | - 182 | 5.95 |
| - 115 | 1.20 | - 149 | 0.70 | - 183 | 4.46 |
| - 116 | 0.32 | - 150 | 3.10 | - 184 | 2.91 |
| - 117 | 2.55 | - 151 | 7.20 | - 185 | 14.05 |
| - 118 | 0.11 | - 152 | 48.20 | - 186 | 23.15 |
| - 119 | 3.00 | - 153 | 17.90 | - 187 | 1.40 |
| - 120 | 0.40 | - 154 | 43.90 | - 188 | 1.86 |
| - 121 | 0.46 | - 155 | 9.20 | - 189 | 10.58 |
| - 122 | 0.10 | - 156 | 13.80 | - 190 | 17.13 |
| - 123 | 0.30 | - 157 | 71.50 | - 191 | 5.51 |
| - 124 | 0.10 | - 158 | 3.47 | - 192 | 40.50 |
| - 125 | 2.90 | - 159 | 0.27 | - 193 | 20.50 |
| - 126 | 0.12 | - 160 | 0.30 | - 194 | 22.60 |
| - 127 | 2.00 | - 161 | 3.40 | - 195 | 0.43 |
| - 128 | 0.11 | - 162 | 0.80 | - 196 | 0.11 |
| - 129 | 0.78 | - 163 | 29.07 | - 197 | 0.98 |
| - 130 | 0.10 | - 164 | 20.49 | - 198 | 0.15 |
| - 131 | 11.36 | - 165 | 22.50 | - 199 | 0.14 |
| - 132 | 0.17 | - 166 | 0.67 | - 200 | 0.88 |
| - 133 | 2.81 | - 167 | 0.50 | - 201 | 25.51 |
| - 134 | 0.71 | - 168 | 12.50 | - 202 | 21.93 |
| - 135 | 12.20 | - 169 | 26.50 | - 203 | 0.12 |
| - 136 | 2.72 | - 170 | 27.50 | - 204 | 15.20 |
| | | | | EP - 205 | 0.82 |
| | | | | - 206 | 0.12 |
| | | | | - 207 | 6.52 |
| | | | | - 208 | 13.12 |
| | | | | - 209 | 2.45 |
| | | | | - 210 | 1.12 |
| | | | | - 211 | 0.61 |
| | | | | - 212 | 1.21 |
| | | | | - 213 | 6.75 |
| | | | | - 214 | 0.13 |
| | | | | - 215 | 3.55 |
| | | | | - 216 | 3.25 |
| | | | | - 217 | 0.25 |
| | | | | - 218 | 1.65 |
| | | | | - 219 | 2.12 |
| | | | | - 220 | 9.86 |

The compounds of this invention also show marked anti-inflammatory activity as measured by their ability to inhibit adjuvant induced polyarthritis in rats. Effect of the compounds of this invention on the development of adjuvant-induced polyarthritis in rats was assayed as follows: Adjuvant arthritis was produced by a single intracutaneous injection of 0.1 ml of the adjuvant mixture containing heat-killed mycobacteria of the human Aoyama B strain suspended in liquid paraffin in 0.6% in the middle part of the distal tail of Sprague Dawley rat (female, 8 weeks old). The compounds suspended in 0.5% carboxymethylcellulose solution protected the animal against the development of lession of adjuvant arthritis by daily oral administration beginning on the day of adjuvant injection and continuing for 24 days thereafter. The activity was measured as the mean inhibition percent for the increase of the hind paw volume of the 8 rats/group on the days 17 and 23 on which the legs become inflamed and reach maximum volumes. The results are shown in Table 2. The compound Nos.

in Table 2 are as defined in Examples as described hereinafter.

TABLE 2

| Compound No. | Dose (mg/kg of body weight) | Inhibition % | |
|---|---|---|---|
| | | 17 days | 23 days |
| EP - 1 | 100 | 82.1 | 77.0 |
| - 2 | 100 | 43.2 | 50.0 |
| - 17 | 100 | 100.0 | 78.7 |
| - 25 | 100 | 52.6 | 77.8 |
| - 26 | 100 | 52.0 | 55.5 |
| - 75 | 100 | 89.6 | 41.0 |
| - 79 | 100 | 64.3 | 90.2 |
| - 81 | 100 | 64.3 | 83.6 |
| - 102 | 100 | 28.0 | 31.0 |
| - 116 | 100 | 35.0 | 33.5 |
| - 121 | 100 | 53.6 | 38.9 |
| - 131 | 100 | 57.1 | 49.2 |
| - 137 | 100 | 40.0 | 38.5 |
| - 143 | 100 | 45.1 | 35.6 |
| - 144 | 100 | 33.3 | 32.1 |
| - 174 | 100 | 30.5 | 29.0 |
| - 175 | 100 | 32.0 | 31.5 |

The pharmaceutical forms contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. The carrier employed may be, for example, either a solid or liquid. Examples of solid carriers are lactose, terra alba, sucrose, talc, gelatin, agar, pectin, acacia, magnesium stearate, stearic acid and the like. Examples of liquid carriers are syrup, peanut oil, olive oil, water and the like. Similarly, the carrier or diluent can include any time delay material well known to the art, such as glyceryl monostearate or glyceryl distearate alone or with a wax.

The compounds of this invention can be used as antiinflammatory agents in dosages of 10–700 mg/kg, preferably 20–100 mg/kg in oral or injectable preparations as described above, to protect mammals against the development of arthritis.

The compounds of this invention are of extremely low toxicity. That is, they hardly show any oral acute toxicity on mice at a dose less than 2 g/kg of body weight. Moreover, no side effect is observed after administration of 1 g/kg/day orally for 30 days for laboratory animals.

The following examples are illustrative of the present invention and are not intended in any way to limit the invention, the scope of which is defined by the appended claims.

EXAMPLE 1

To a solution of 3.0 g (0.026 mole) of cyclohexanol and 2.1 g (0.026 mole) of pyridine dissolved in 50 ml of ethyl ether, a solution of 2.52 g (0.015 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give dicyclohexyl epoxysuccinate (EP-1) as an oil. Yield 3.3 g (75%), b.p. 225°–227° C. (6 mmHg).

EXAMPLE 2

(a) To a solution of 2.5 g (0.0085 mole) of dicyclohexyl epoxysuccinate dissolved in 40 ml of cyclohexanol, a solution of 0.4 g of potassium hydroxide dissolved in 3 ml of methanol was added dropwise at room temperature. After the mixture had been stirred for 2 hours, to this, 300 ml of ethyl ether was added. Then, the mixture was allowed to stand overnight at about 5° C. The precipitate thus formed was filtered and recrystallized from ethanol-ether mixture to give cyclohexyl potassium epoxysuccinate (EP-2) as colorless needles. Yield 1.2 g (48%), m.p. 187°–189° C.

(b) To a solution of 1.0 g (0.0034 mole) of dicyclohexyl epoxysuccinate dissolved in 30 ml of dimethylformamide, 2 ml of aqueous 1 N potassium hydroxide solution was added dropwise while being stirred and cooled at 0° C. After 10 min., the mixture was filtered. Then, to the solution, 400 ml of acetone was added and the mixture was allowed to stand for a while. The resulting crystals were recrystallized from water-acetone to give cyclohexyl potassium epoxysuccinate (EP-2) as colorless needles. Yield 0.74 g (74%), m.p. 188°–190° C.

EXAMPLE 3

To a solution of 3.0 g (0.026 mole) of 2-cis-methylcyclohexanol, and 2.1 g (0.026 mole) of pyridine dissolved in 50 ml of ethyl ether, a solution of 2.52 g (0.015 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexaneacetone (10:1) mixture as solvent to give di-2'-cis-methylcyclohexyl epoxysuccinate (EP-3) as an oil. Yield 3.3 g (77%). IR$\nu_{KBr}$(cm$^{-1}$): 1740 (ester,-carbonyl), 900 (epoxide). NMR(CDCl$_3$)δ: 0.87 (6H,d,J=6 Hz), 1.10–2.00 (18H, b.s.), 3.61 (2H, s), 5.00 (2H,b.s.).

The following compounds were obtained from the corresponding materials by method similar to that described in Example 3.

di-2'-trans-methylcyclohexyl epoxysuccinate(EP-5),
di-2'-trans-chlorocyclohexyl epoxysuccinate(EP-7),
di-3'-cis-bromocyclohexyl epoxysuccinate(EP-9),
di-2'-cis-bromo-5'-trans-chlorocyclohexyl epoxysuccinate(EP-11),
di-2',6'-trans-dimethylcyclohexyl epoxysuccinate(EP-13)

EXAMPLE 4

To a solution of 5.0 g (0.016 mole) of di-2'-cis-methylcyclohexyl epoxysuccinate dissolved in 50 ml of dimethylformamide, 5.14 ml of aqueous 3 N potassium hydroxide solution was added dropwise while being stirred and cooled at 0° C. After the mixture had been stirred for 10 to 15 min., to this, 1000 ml of acetone was added. The formed crystals were filtered and recrystallized from acetone-water to give 2'-cis-methylcyclohexyl potassium epoxysuccinate(EP-4) as colorless crystals. Yield 0.6 g (15%), m.p.>300° C.(d.). IR$\nu_{KBr}$(cm$^{-1}$): 1740 (ester, carbonyl), 1620 (COOK), 900 (epoxide). NMR(D$_2$O)δ: 1.20–2.25 (9H, m), 2.26 (3H, s), 3.45, 3.55 (2H, d.d., J=2 Hz), 4.95 (1H,m).

The following compounds were obtained from the corresponding materials by methods similar to that described in Example 4.
- 2'-trans-methylcyclohexyl potassium epoxysuccinate(EP-6),
- 2'-trans-chlorocyclohexyl potassium epoxysuccinate(EP-8),
- 3'-cis-bromocyclohexyl potassium epoxysuccinate(EP-10),
- 2'-cis-bromo-5'-trans-chlorocyclohexyl potassium epoxysuccinate(EP-12),
- 2',6'-trans-dimethylcyclohexyl potassium epoxysuccinate(EP-14).

EXAMPLE 5

To a solution of 3.0 g (0.026 mole) of 4-trans-methylcyclohexanol and 2.1 g (0.026 mole) of pyridine dissolved in 50 ml of ethyl ether, a solution of 2.52 g (0.015 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give di-4'-trans-methylcyclohexyl epoxysuccinate(EP-15) as an oil. Yield 3.8 g (88%). IR$\nu_{KBr}$(cm$^{-1}$): 1745 (ester, carbonyl), 900 (epoxide). NMR(CDCl$_3$)δ: 0.88 (6H, b.s.), 1.00–2.16 (18H, m), 3.52 (2H, s), 4.69 (2H, b.s.).

The following compounds were obtained from the corresponding materials by methods similar to that described in Example 5.
- di-4'-cis-methylcyclohexyl epoxysuccinate(EP-17),
- di-4'-trans-chlorocyclohexyl epoxysuccinate(EP-19),
- di-3'-cis-chloro-trans-4'-bromocyclohexyl epoxysuccinate(EP-21),
- di-3',5'-trans-dichlorocyclohexyl epoxysuccinate(EP-23).

EXAMPLE 6

To a solution of 5.0 g (0.016 mole) of di-4'-trans-methylcyclohexyl epoxysuccinate dissolved in 50 ml of dimethylformamide, 5.14 ml of aqueous 3 N potassium hydroxide solution was added dropwise while being stirred and cooled at 0° C. After the mixture had been stirred for 10 to 15 min., to this, 1000 ml of acetone was added. The formed crystals were filtered and recrystallized from acetone-water to give 4'-trans-methylcyclohexyl potassium epoxysuccinate(EP-16) as colorless crystals. Yield 0.7 g (17%), m.p.>300° C.(d.). IR$\nu_{KBr}$(cm$^{-1}$): 1745 (ester, carbonyl), 1618 (COOK), 902 (epoxide). NMR (D$_2$O)δ: 1.0–2.3 (9H, m), 2.25 (3H, s), 3.40, 3.51 (2H, d.d., J=2 Hz), 4.76 (1H, m).

The following compounds were obtained from the corrsponding materials by methods similar to that described in Example 6.
- 4'-cis-methylcyclohexyl potassium epoxysuccinate(EP-18),
- 4'-trans-chlorocyclohexyl potassium epoxysuccinate(EP-20),
- 3'-cis-chloro-4'-trans-bromocyclohexyl potassium epoxysuccinate(EP-22),
- 3',5'-trans-dichlorocyclohexyl potassium epoxysuccinate(EP-24).

EXAMPLE 7

To a solution of 3.0 g (0.026 mole) of cyclopentanol and 2.1 g (0.026 mole) of pyridine dissolved in 50 ml of ethyl ether, a solution of 2.52 g (0.015 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give dicyclopentyl epoxysuccinate(EP-25) as an oil. Yield 3.6 g (77%), b.p. 221°–223° C. (6 mmHg).

The following compound was obtained from the corresponding material by methods similar to that described in Example 7.
- dicyclopropyl epoxysuccinate(EP-27).

EXAMPLE 8

(a) When a procedure as described in Example 2(a) was carried out by using dicyclopentyl epoxysuccinate (2.5 g) and cyclopentanol (40 ml) instead of dicyclohexyl epoxysuccinate and cyclohexanol, respectively, cyclopentyl potassium epoxysuccinate(EP-26) was obtained as crystals. Yield 1.2 g (48%), m.p. 157°–160° C. (from water-acetone).

(b) When a procedure as described in Example 2(b) was carried out by using dicyclopentyl epoxysuccinate (1.0 g) instead of dicyclohexyl epoxysuccinate, cyclopentyl potassium epoxysuccinate(EP-26) was obtained as crystals. Yield 0.68 g (68%), m.p. 157°–160° C. (from water-acetone).

The following compound was obtained from the corresponding material by a method as described in Example 8(b).
- cyclopropyl potassium epoxysuccinate(EP-28).

EXAMPLE 9

To a solution of 3.0 g (0.026 mole) of 3-cis-chlorocyclopentanol and 2.1 g (0.026 mole) of pyridine dissolved in 50 ml of ethyl ether, a solution of 2.52 g (0.015 mole) of epoxysuccinyl chloride dissolved in 5 ml of ethyl ether was added dropwise while being stirred and cooled at 0° to −5° C. Then, when a procedure as described in Example 7 was carried out, di-3'-cis-chlorocyclopentyl epoxysuccinate(EP-29) was obtained as an oil. Yield 3.5 g (85%), m.p.>300° C.(d.). IR$\nu_{KBr}$(cm$^{-1}$): 1745 (ester, carbonyl), 901 (epoxide). NMR(CDCl$_3$)δ: 0.90–2.50 (14H, m), 3.60 (2H, s), 4.86 (2H, b.s.).

The following compounds were obtained from the corresponding materials by methods similar to that described in Example 9.
- di-3'-trans-methylcyclopentyl epoxysuccinate(EP-31),
- di-2'-trans-bromocyclopentylepoxysuccinate(EP-33).

EXAMPLE 10

When a procedure as described in Example 6(b) was carried out by using di-3'-cis-chlorocyclopentyl epoxysuccinate (1.0 g) instead of dicyclopentyl epoxysuccinate, 3'-cis-chlorocyclopentyl potassium epoxysuccinate(EP-30) was obtained as crystals. Yield 0.52 g (52%), m.p. 164°–170° C.(d.).

The following compounds were obtained from the corresponding materials by methods similar to that described in Example 10.

3'-trans-methylcyclopentyl potassium epoxysuccinate(EP-32),
    2'-trans-bromocyclopentyl potassium epoxysuccinate(EP-34).

EXAMPLE 11

To a solution of 3.0 g (0.023 mole) of cyclooctanol and 1.8 g (0.023 mole) of pyridine dissolved in 50 ml of ethyl ether, a solution of 2.35 g (0.014 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give dicyclooctyl epoxysuccinate(EP-35) as an oil. Yield 3.4 g (88%). IR$\nu_{KBr}$(cm$^{-1}$): 1740 (ester, carbonyl), 898 (epoxide). NMR(CDCl$_3$)$\delta$: 1.20–2.05 (28H, m), 3.55 (2H, s), 5.00 (2H, b.s.).

EXAMPLE 12

To a solution of 5.0 g (0.016 mole) of dicyclooctyl epoxysuccinate dissolved in 50 ml of dimethylformamide, 5.14 ml of aqueous 3 N potassium hydroxide solution was added dropwise while being stirred and cooled at 0° C. After the mixture had been stirred for 10 to 15 min., to this, 1000 ml of acetone was added. The formed crystals were filtered and recrystallized from water-acetone to give cyclooctyl potassium epoxysuccinate(EP-36) as colorless crystals. Yield 0.5 g (14%), m.p.>300° C.(d.). IR$\nu_{KBr}$(cm$^{-1}$): 1740 (ester, carbonyl), 1610 (COOK), 900 (epoxide). NMR (D$_2$O)$\delta$: 1.20–2.05 (14H, m), 3.49,3.51 (2H, d.d., J=2 Hz), 4.79 (1H, m).

EXAMPLE 13

To a solution of 3.0 g (0.02 mole) of 2-adamantanol and 1.6 g (0.02 mole) of pyridine dissolved in 50 ml of ethyl ether, a solution of 2.0 g (0.012 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give di-2-adamantyl epoxysuccinate(EP-37) as colorless crystals. Yield 3.1 g (79%), m.p. 152°–154° C. (from n-hexane-acetone).

EXAMPLE 14

To a solution of 5.0 g (0.016 mole) of di-2-adamantyl epoxysuccinate dissolved in 50 ml of dimethylformamide, 5.14 ml of aqueous 3 N potassium hydroxide solution was added dropwise while being stirred and cooled at 0° C. When the mixture was treated by the method as described in Example 12, 2-adamantyl potassium epoxysuccinate(EP-38) was obtained as colorless crystals. Yield 0.5 g (14%), m.p.>300° C.(d.). IR$\nu_{KBr}$(cm$^{-1}$): 1740 (ester, carbonyl), 1618 (COOK), 900 (epoxide). NMR(D$_2$O)$\delta$: 1.0–2.5 (14H, m), 3.49, 3.51 (2H, d.d., J=2 Hz), 5.00 (1H, m).

EXAMPLE 15

To a solution of 0.8 g (0.011 mole) of cyclopropanemethanol and 0.87 g (0.011 mole) of pyridine dissolved in 30 ml of ethyl ether, a solution of 1.0 g (0.0006 mole) of epoxysuccinyl chloride dissolved in 3 ml of ethyl ether was added dropwise while being stirred and cooled at 0° to −5° C. After the mixture had been stirred for 30 to 50 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give dicyclopropanemethyl epoxysuccinate(EP-39) as an oil. Yield 1.1 g (83%). Mass: m/e 240 (M+). IR$\nu_{KBR}$(cm$^{-1}$): 1750 (ester, carbonyl), 901 (epoxide). NMR(CDCl$_3$)$\delta$: 0.20–1.50 (10H, m), 4.64 (2H, s), 4.99 (4H, d, J=7.2 Hz).

EXAMPLE 16

To a solution of 0.63 g (0.003 mole) of dicyclopropanemethyl epoxysuccinate dissolved in 10 ml of dimethylformamide, one ml of aqueous 3 N potassium hydroxide solution was added dropwise while being stirred and cooled at 0° C. After the mixture had been stirred for 10 to 15 min., to this, 500 ml of acetone was added. The formed crystals were filtered and recrystallized from acetone-water to give cyclopropanemethyl potassium epoxysuccinate(EP-40) as colorless crystals. Yield 0.15 g (26%), m.p.>300° C.(d). IR$\nu_{KBr}$(cm$^{-1}$): 1745 (ester, carbonyl), 1610 (COOK), 900 (epoxide). NMR(D$_2$O)$\delta$: 0.20–1.40 (5H, m), 3.45, 3.58 (2H, d.d., J=2 Hz), 4.00 (2H, d., J=6 Hz).

EXAMPLE 17

To a solution of 3.0 g (0.026 mole) of cyclohexanemethanol and 2.1 g (0.026 mole) of pyridine dissolved in 50 ml of ethyl ether, a solution of 2.52 g (0.015 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered. The ethyl ether layer thus obtained was washed with water, dried over anhydrous sodium sulfate and distilled to dryness. The resulting residue was chromatographed on silica gel using n-hexane-acetone (10:1) mixture as solvent to give dicyclohexanemethyl epoxysuccinate(EP-41) as an oil. Yield 3.6 g (84%), b.p. 238°–240° C. (6 mmHg).

The following compounds were obtained from the corresponding materials by methods similar to that described in Example 17.

dicyclopentanemethyl epoxysuccinate(EP-43),
    di-1-cyclopentaneethyl epoxysuccinate(EP-45),
    di-1-adamantanemethyl epoxysuccinate(EP-47),
    di-2-(1-adamantane)ethyl epoxysuccinate(EP-49),
    dibicyclo [2,2,2] octyl epoxysuccinate(EP-51),
    dibornyl epoxysuccinate(EP-53),
    dinorbornyl epoxysuccinate(EP-55),
    dinorbor-5-en-2-yl epoxysuccinate(EP-57).

EXAMPLE 18

To a solution of 5.0 g (0.015 mole) of dicyclohexanemethyl epoxysuccinate dissolved in 50 ml of dimethylformamide, 5.14 ml of aqueous 3 N potassium hydroxide solution was added dropwise while being stirred and cooled at 0° C. After the mixture had been stirred for 10 to 15 min., to this, 1000 ml of acetone was added. The formed crystals were filtered and recrystallized from acetone-water to give cyclohexanemethyl potassium epoxysuccinate(EP-42) as colorless crystals. Yield 0.8 g (19%), mp.>300° C. (d.). IR$\nu_{KBr}$(cm$^{-1}$): 1740 (ester, carbonyl), 1620 (COOK), 900 (epoxide). NMR(D$_2$O)δ: 1.0–2.3 (10H, m), 3.94, 3.51 (2H, d.d., J=2 Hz), 4.85 (1H, m).

The following compounds were obtained from the corresponding materials by the similar method as described in Example 18.

cyclopentanemethyl potassium epoxysuccinate(EP-44),
1-cyclopentaneethyl potassium epoxysuccinate(EP-46),
1-adamantanemethyl potassium epoxysuccinate(EP-48), 2-(1-adamantane)ethyl potassium epoxysuccinate(EP-50),
bicyclo [2,2,2] octyl potassium epoxysuccinate(EP-52),
bornyl potassium epoxysuccinate(EP-54),
norbornyl potassium epoxysuccinate(EP-56),
norbor-5-en-2-yl potassium epoxysuccinate(EP-58).

EXAMPLE 19

To a solution of 3.0 g (0.026 mole) of 2-cyclopentaneethanol and 2.1 g (0.026 mole) of pyridine dissolved in 50 ml of ethyl ether, a solution of 2.52 g (0.015 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give di-2-cyclopentaneethyl epoxysuccinate(EP-59) as an oil. Yield 3.2 g (74%).

IR$\nu_{KBr}$(cm$^{-1}$): 1750 (ester, carbonyl), 900 (epoxide). NMR(CDCl$_3$)δ: 0.80–2.10 (22H, m), 3.62 (2H, s), 4.18 (4H, t, J=6.7 Hz).

The following compound was obtained from the corresponding material by the similar method as described in Example 19.

di-2-cyclohexaneethyl epoxysuccinate(EP-61).

EXAMPLE 20

To a solution of 5.0 g (0.015 mole) of di-2-cyclopentaneethyl epoxysuccinate dissolved in 50 ml of dimethylformamide, 5.14 ml of aqueous 3 N potassium hydroxide solution was added dropwise while being stirred and cooled at 0° C. After the mixture had been stirred for 10 to 15 min., to this, 1000 ml of acetone was added. The formed crystals were filtered and recrystallized from acetone-water to give 2-cyclopentaneethyl potassium epoxysuccinate(EP-60) as colorless crystals. Yield 1.1 g (27%), m.p.>300° C.(d.). IR$\nu_{KBr}$(cm$^{-1}$): 1740 (ester, carbonyl), 1610 (COOK), 900 (epoxide). NMR(D$_2$O)δ: 0.90–2.10 (11H, m), 3.44, 3.56 (2H, d.d., J=2 Hz), 4.18 (2H, t, J=6.7 Hz).

The following compound was obtained from the corresponding material by a method similar to that described in Example 20.

2-cyclohexaneethyl potassium epoxysuccinate(EP-62).

EXAMPLE 21

To a solution of 3.0 g (0.023 mole) of 3-cyclopentanepropanol and 1.82 g (0.023 mole) of pyridine dissolved in 50 ml of ethyl ether, a solution of 2.0 g (0.012 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered. The ethyl ether layer thus obtained was washed with water, dried over anhydrous sodium sulfate and distilled to dryness. The resulting residue was chromatographed on silica gel using n-hexane-acetone (10:1) mixture as solvent to give di-3-cyclopentanepropyl epoxysuccinate(EP-63) as an oil. Yield 3.8 g (83%). IR$\nu_{KBr}$(cm$^{-1}$): 1750 (ester, carbonyl), 900 (epoxide). NMR(CDCl$_3$)δ: 0.88–2.00 (26H, m), 3.12 (2H,s), 4.16 (4H, t, J=6.7 Hz).

The following compounds were obtained from the corresponding materials by methods similar to that described in Example 21.

di-3-cyclohexanepropyl epoxysuccinate(EP-65),
di-4-cyclohexanebutyl epoxysuccinate(EP-67).

EXAMPLE 22

To a solution of 5.0 g (0.014 mole) of di-3-cyclopentanepropyl epoxysuccinate dissolved in 50 ml of dimethylformamide, 5.14 ml of aqueous 3 N potassium hydroxide solution was added dropwise while being stirred and cooled at 0° C. After the mixture had been stirred for 10 to 15 min., to this, 1000 ml of acetone was added. The formed crystals were filtered and recrystallized from acetone-water to give 3-cyclopentanepropyl potassium epoxysuccinate(EP-64) as colorless crystals. Yield 0.5 g (13%), m.p.>300° C.(d.). IR$\nu_{KBr}$(cm$^{-1}$): 1730 (ester, carbonyl), 1610 (COOK), 900 (epoxide). NMR(D$_2$O)δ: 0.80–2.10 (13H, m), 3.44, 3.56 (2H, d.d., J=2 Hz), 4.15 (2H, t, J=6.7 Hz).

The following compounds were obtained from the corresponding materials by a method similar to that described in Example 22.

3-cyclohexanepropyl potassium epoxysuccinate(EP-66),
4-cyclohexanebutyl potassium epoxysuccinate(EP-68).

EXAMPLE 23

To a solution of 3.0 g (0.027 mole) of 3-cyclohexane methanol and 2.1 g (0.027 mole) of pyridine dissolved in 50 ml of ethyl ether, a solution of 2.52 g (0.015 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give di-3-cyclohexenemethyl epoxysuccinate(EP-69) as an oil. Yield 3.5 g (81%). IR$\nu_{KBr}$(cm$^{-1}$): 1750 (ester, cabonyl), 900 (epoxide). NMR(CDCl$_3$)δ: 1.10–2.50 (14H, m), 3.64 (2H, s), 4.07 (4H, d, J=7.2 Hz), 5.64 (4H, s).

The following compounds were obtained from the corresponding materials by a method similar to that described in Example 23.

di-2-cyclopentenemethyl epoxysuccinate(EP-71),
di-4-cyclooctenemethyl epoxysuccinate(EP-73).

EXAMPLE 24

To a solution of 5.0 g (0.016 mole) of di-3-cyclohexenemethyl epoxysuccinate dissolved in 50 ml of dimethylformamide, 5.14 ml of aqueous 3 N potassium hydroxide solution was added dropwise while being stirred and cooled at 0° C. After the mixture had been stirred for 10 to 15 min., to this, 1000 ml of acetone was added. The formed crystals were filtered and recrystallized from acetone-water to give 3-cyclohexenemethyl potassium epoxysuccinate(EP-70) as colorless crystals. Yield 0.7 g (17%), m.p.>300° C.(d.). IR$\nu_{KBr}$(cm$^{-1}$): 1740 (ester, carbonyl), 1610 (COOK), 900 (epoxide). NMR(D$_2$O)δ: 1.00-2.30 (7H, m), 3.45, 3.58 (2H, d.d., J=2 Hz), 4.07 (2H, d, J=6 Hz), 5.66 (2H, s).

The following compounds were obtained from the corresponding materials by methods similar to that described in Example 24.

2-cyclopentenemethyl potassium epoxysuccinate(EP72), 4-cyclooctenemethyl potassium epoxysuccinate(EP-74).

EXAMPLE 25

To a solution of 3.0 g (0.029 mole) of tetrahydrofurfuryl alcohol (tetrahydro-2-furanmethanol) and 2.3 g (0.029 mole) of pyridine dissolved in 50 ml of ethyl ether, a solution of 2.6 g (0.016 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give di-tetrahydro-2-furanmethyl epoxysuccinate(EP-75) as an oil. Yield 3.2 g (73%), b.p. 221°-224° C. (6 mmHg).

The following compound was obtained from the corresponding material by a method similar to that described in Example 25.

di-2-furanmethyl epoxysuccinate(EP-77).

EXAMPLE 26

To a solution of 5.0 g (0.016 mole) of di-tetrahydro-2-furanmethyl epoxysuccinate dissolved in 50 ml of dimethylformamide, 5.14 ml of aqueous 3 N potassium hydroxide solution was added dropwise while being stirred and cooled at 0° C. After the mixture had been stirred for 10 to 15 min., to this, 1000 ml of acetone was added. The formed crystals were filtered and recrystallized from acetone-water to give tetrahydro-2-furanmethyl potassium epoxysuccinate(EP-76) as colorless crystals. Yield 0.6 g (16%), m.p.>300° C.(d.). IR$\nu_{KBr}$(cm$^{-1}$): 1740 (ester, carbonyl), 1610 (COOK), 901 (epoxide). NMR(D$_2$O)δ: 1.00-2.3 (6H, m), 3.42, 3.51 (2H, d.d., J=2 Hz), 4.20 (2H, t, J=6 Hz).

The following compound was obtained from the corresponding material by a method similar to that described in Example 26.

2-furanmethyl potassium epoxysuccinate(EP-78).

EXAMPLE 27

To a solution of 3.0 g (0.029 mole) of 2-thenyl alcohol (2-thiofuranmethanol) and 2.3 g (0.029 mole) of pyridine dissolved in 50 ml of ethyl ether, a solution of 2.6 g (0.016 mole) of epoxysuccinyl chloride dissolved in 5 ml of ethyl ether was added dropwise while being stirred and cooled at 0° to −5° C. Then, when a procedure as described in Example 25 was carried out, di-2-thenyl epoxysuccinate(EP-79) was obtained as an oil. Yield 3.3 g (82%), m.p.>300° C.(d.). Mass: m/e 324 (M+). IR$\nu_{KBr}$(cm$^{-1}$): 1750 (ester, carbonyl), 900 (epoxide). NMR(CDCl$_3$)δ: 3.75 (2H, s), 5.41 (4H, s), 6.95-7.85 (6H, m).

EXAMPLE 28

When a procedure as described in Example 26 was carried out by using di-2-thenyl epoxysuccinate (1.9 g) instead of di-tetrahydro-2-furanmethyl epoxysuccinate, 2'-thenyl potassium epoxysuccinate(EP-80) was obtained as colorless crystals from water-acetone. Yield 0.90 g (47.6%), m.p.>300° C.(d.). IR$\nu_{KBr}$(cm$^{-1}$): 1745 (ester, carbonyl), 1620 (COOK), 902 (epoxide). NMR(D$_2$O)δ: 3.44, 3.56 (2H, d.d., J=2 Hz), 5.40 (2H, s), 6.96-7.35 (2H, m), 7.35-7.60 (1H, m).

EXAMPLE 29

To a solution of 3.0 g (0.025 mole) of 1-naphthylmethanol and 2.0 g (0.025 mole) of pyridine dissolved in 50 ml of ethyl ether, a solution of 2.35 g (0.014 mole) of epoxysuccinyl chloride dissolved in 5 ml of ethyl ether was dropped while being stirred and cooled at 0° to −5° C. Then, when a procedure as described in Example 23 was carried out, di-1'-naphthylmethyl epoxysuccinate(EP-81) was obtained as colorless needles. Yield 3.4 g (86%), m.p. 105°-107° C. (from n-hexane-acetone).

The following compounds were obtained from the corresponding materials by the method as described in Example 29.

di-2'-chloro-1'-naphthylmethyl epoxysuccinate(EP-83), di-5'-bromo-1'-naphthylmethyl epoxysuccinate(EP-85), di-4',5'-dimethyl-1'-naphthylmethyl epoxysuccinate(EP-87).

EXAMPLE 30

When the procedure as described in Example 18 was carried out by using di-1'-naphthylmethyl epoxysuccinate (1.9 g) instead of dicyclohexanemethyl epoxysuccinate, 1'-naphthylmethyl potassium epoxysuccinate(EP-82) was obtained as colorless crystals from water-acetone. Yield 0.92 g (45%), m.p. 185°-188° C.

The following compounds were obtained from the corresponding materials by methods similar to that described in Example 30.

2'-chloro-1'-naphthylmethyl potassium epoxysuccinate(EP-84),

5'-bromo-1'-naphthylmethyl potassium epoxysuccinate(EP-86),

4',5'-dimethyl-1'-naphthylmethyl potassium epoxysuccinate(EP-88).

EXAMPLE 31

To a solution of 3.0 g (0.025 mole) of p-methylbenzyl alcohol and 2.0 g (0.025 mole) of pyridine dissolved in 50 ml of ethyl ether, a solution of 2.2 g (0.013 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give di-p-methylbenzyl epoxysuccinate(EP-89) as colorless crystals. Yield 3.5 g (84%), m.p. 17° C. (from n-hexane-acetone).

The following compounds were obtained from the corresponding materials by a method as described in Example 31.
  di-o-methylbenzyl epoxysuccinate(EP-91),
  di-3',5'-dimethylbenzyl epoxysuccinate(EP-93),
  di-2',4',6'-trimethylbenzyl epoxysuccinate(EP-95),
  di-2'-bromo-3'-methylbenzyl epoxysuccinate(EP-97),
  di-3'-trifluoromethylbenzyl epoxysuccinate(EP-99).

EXAMPLE 32

To a solution of 1.9 g (0.0056 mole) of di-p-methylbenzylepoxysuccinate dissolved in 19 ml of dimethylformamide, 2.0 ml of aqueous 3 N potassium hydroxide solution was added dropwise while being stirred and cooled at 0° C. After the mixture had been stirred for 10 to 15 min., to this, 200 ml of acetone was added. The formed crystals were filtered and recrystallized from water-acetone to give p-methylbenzyl potassium epoxysuccinate (EP-90) as colorless crystals. Yield 0.80 g (46%), m.p. 177°–181° C.(d.).

The following compounds were obtained from the corresponding materials by the similar method as described in Example 32.
  o-methylbenzyl potassium epoxysuccinate(EP-92),
  3',5'-dimethylbenzyl potassium epoxysuccinate(EP-94),
  2',4',6'-trimethylbenzyl potassium epoxysuccinate(EP-96),
  2'-bromo-3'-methylbenzyl potassium epoxysuccinate(EP-98),
  3'-trifluoromethylbenzyl potassium epoxysuccinate(EP-100).

EXAMPLE 33

To a solution of 3.0 g (0.022 mole) of p-methoxybenzyl alcohol and 1.74 g (0.022 mole) of pyridine dissolved in 50 ml of ethyl ether, a solution of 1.85 g (0.011 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give di-p-methoxybenzyl epoxysuccinate(EP-101) as colorless needles. Yield 3.1 g (78%), m.p. 82°–84° C. (from n-hexane-acetone).

The following compound was obtained from the corresponding material by a method as described in Example 33.
  di-methylene-3',4'-dioxybenzyl epoxysuccinate(EP-103).

EXAMPLE 34

To a solution of 1.9 g (0.0051 mole) of di-p-methoxybenzyl epoxysuccinate dissolved in 19 ml of dimethylformamide, 2.0 ml of aqueous 3 N potassium hydroxide solution was added dropwise while being stirred and cooled at 0° C. After the mixture had been stirred for 10 to 15 min., to this, 200 ml of acetone was added. The formed crystals were filtered and recrystallized from water-acetone to give p-methoxybenzyl potassium epoxysuccinate (EP-102) as colorless needles. Yield 0.95 g (47%), m.p. 189°–193° C.(d.).

The following compound was obtained from the corresponding material by a method as described in Example 34.
  methylene-3',4'-dioxybenzyl potassium epoxysuccinate(EP-104)

EXAMPLE 35

To a solution of 3.0 g (0.013 mole) of o-iodobenzyl alcohol and 1.0 g (0.013 mole) of pyridine dissolved in 50 ml of ethyl ether, a solution of 1.2 g (0.007 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give di-o-iodobenzyl epoxysuccinate(EP-105) as colorless needles. Yield 3.0 g (83%), m.p. 111°–112° C.

The following compounds were obtained from the corresponding materials by a method as described in Example 35.
  di-o-chlorobenzyl epoxysuccinate(EP-107),
  di-m-chlorobenzyl epoxysuccinate(EP-109),
  di-p-iodobenzyl epoxysuccinate(EP-111),
  di-p-bromobenzyl epoxysuccinate(EP-113),
  di-p-chlorobenzyl epoxysuccinate(EP-115),
  di-2',4'-dichlorobenzyl epoxysuccinate(EP-117),
  di-2'-bromo-4'-iodobenzyl epoxysuccinate(EP-119).

EXAMPLE 36

To a solution of 4.5 g (0.008 mole) of di-o-iodobenzyl epoxysuccinate dissolved in 35 ml of dimethylformamide, 2.7 ml of aqueous 3 N potassium hydroxide solution was added dropwise while being stirred and cooled at 0° C. After the mixture had been stirred for 10 to 15 min., to this, 500 ml of acetone was added. The formed crystals were filtered and recrystallized from water-acetone to give o-iodobenzyl potassium epoxysuccinate(EP-106) as a colorless amorphous solid. Yield 0.9 g (29%). IR$\nu_{KBr}$(cm$^{-1}$): 1718 (ester, carbonyl), 1610 (COOK), 900 (epoxide). NMR(D$_2$O)δ: 3.48, 3.62 (2H,d.d., J=2 Hz), 5.14 (2H, s), 6.87–7.52 (4H, m).

The following compounds were obtained from the corresponding materials by a method as described in Example 36.
  o-chlorobenzyl potassium epoxysuccinate(EP-108),
  m-chlorobenzyl potassium epoxysuccinate(EP-110),
  p-iodobenzyl potassium epoxysuccinate(EP-112),
  p-bromobenzyl potassium epoxysuccinate(EP-114),
  p-chlorobenzyl potassium epoxysuccinate(EP-116),
  2',4'-dichlorobenzyl potassium epoxysuccinate(EP-118),
  2'-bromo-4'-iodobenzyl potassium epoxysuccinate(EP-120).

EXAMPLE 37

To a solution of 3.0 g (0.024 mole) of m-fluorobenzyl alcohol and 1.9 g (0.024 mole) of pyridine dissolved in 50 ml of ehtyl ether, a solution of 2.0 g (0.012 mole) of epoxysuccinyl chloride dissolved in 5 ml of ethyl ether was added dropwise while being stirring and cooling at 0° to −5° C. After the mixture had been stirred for 30 to 60 min., the precipitated hydrogen chloride salt of pyridine was filtered out. The ethyl ether layer thus obtained was washed with water, dried over anhydrous sodium sulfate and distilled to dryness. The resulting residue was chromatographed on silica gel using n-hexane-acetone (10:1) mixture as solvent to give di-m-fluorobenzyl epoxysuccinate(EP-121) as an oil. Yield 3.1 g (75%). IR$\nu_{KBr}$(cm$^{-1}$): 1720 (ester, carbonyl), 899 (epoxide). NMR(CDCl$_3$)δ: 3.52 (2H, s), 5.10 (4H, s), 6.87-7.52 (8H, m).

The following compounds were obtained from the corresponding materials by a method as described in Example 37.

di-o-fluorobenzyl epoxysuccinate(EP-123),
di-3'-chloro-4'-bromobenzyl epoxysuccinate(EP-125),
di-2',5'-dichlorobenzyl epoxysuccinate(EP-127).

EXAMPLE 38

To a solution of 5.0 g (0.0114 mole) of di-m-fluorobenzyl epoxysuccinate dissolved in 35 ml of dimethylformamide, 4.8 ml of aqueous 3 N potassium hydroxide solution was added dropwise while being stirred and cooled at 0° C. After the mixture had been stirred for 10 to 15 min., to this, 500 ml of acetone was added. The formed crystals were filtered and recrystallized from water-acetone to give m-fluorobenzyl potassium epoxysuccinate(EP-122) as a colorless amorphous solid. Yield 1.1 g (25%). IR$\nu_{KBr}$(cm$^{-1}$): 1740 (ester, carbonyl), 1610 (COOK), 900 (epoxide). NMR(D$_2$O)δ:3.48, 3.62 (2H, d.d., J=2 Hz), 5.14 (2H, s), 6.85-7.52 (4H, m).

The following compounds were obtained from the corresponding materials by a method as described in Example 38.

o-fluorobenzyl potassium epoxysuccinate(EP-124),
3'-chloro-4'-bromobenzyl potassium epoxysuccinate(EP-126),
2',5'-dichlorobenzyl potassium epoxysuccinate(EP-128).

EXAMPLE 39

To a solution of 3.0 g (0.025 mole) of 2-phenylethanol and 2.0 g (0.025 mole) of pyridine dissolved in 50 ml of ethyl ether, a solution of 2.35 g (0.014 mole) of epoxysuccinyl chloride dissolved in 5 ml of ethyl ether was added dropwise while being stirred and cooled at 0° to −5° C. After the mixture had been stirred for 30 to 60 min., the precipitated hydrogen chloride salt of pyridine was filtered. The ethyl ether layer thus obtained was washed with water, dried over anhydrous sodium sulfate and distilled to dryness. The resulting residue was chromatographed on silica gel using n-hexane-acetone (10:1) mixture as solvent to give di-2'-phenylethyl epoxysuccinate(EP-129) as an oil. Yield 3.2 g (79%). IR$\nu_{KBr}$(cm$^{-1}$): 1750 (ester, carbonyl), 901 (epoxide). NMR(CDCl$_3$)δ: 2.93 (4H, t, J=6.7 Hz), 3.50 (2H, s), 4.36 (4H, t, J=6.7 Hz), 7.17 (10H, s).

The following compound was obtained from the corresponding materials by a method as described in Example 39.

di-3'-phenylpropyl epoxysuccinate(EP-131).

EXAMPLE 40

To a solution of 3.3 g (0.01 mole) of di-2'-phenylethyl epoxysuccinate dissolved in 30 ml of dimethylformamide, 3.3 ml of aqueous 3 N potassium hydroxide solution was added dropwise while being stirred and cooled at 0° C. After the mixture had been stirred for 10 to 15 min., to this, 1000 ml of acetone was added. The formed crystals were filtered and recrystallized from acetone-water to give 2'-phenylethyl potassium epoxysuccinate(EP-130) as colorless crystals. Yield 0.85 g (38%), m.p. >300° C.(d.). IR$\nu_{KBr}$(cm$^{-1}$): 1745 (ester, carbonyl), 1610 (COOK), 900 (epoxide). NMR(D$_2$O)δ: 0.70-2.00 (13H, m), 3.41, 3.53 (2H, d.d., J=2 Hz), 4.20 (2H, t, J=6 Hz).

The following compound was obtained from the corresponding material by the method as described in Example 40.

3'-phenylpropyl potassium epoxysuccinate(EP-132).

EXAMPLE 41

To a solution of 3.0 g (0.025 mole) of 3-phenyl-2-propen-1-ol (cinnamyl alcohol) and 2.0 g (0.025 mole) of pyridine dissolved in 50 ml of ethyl ether, a solution of 2.35 g (0.014 mole) of epoxysuccinyl chloride dissolved in 5 ml of ethyl ether was added dropwise while being stirred and cooled at 0° to −5° C. Then, when the procedure as described in Example 39 was carried out, di-3'-phenyl-2'-propenyl epoxysuccinate(EP-133) was obtained as colorless needles. Yield 3.1 g (78%), m.p. 165° C. (from n-hexane-acetone).

EXAMPLE 42

When the procedure as described in Example 40 was carried out by using di-3'-phenyl-2'-propenyl epoxysuccinate (1.9 g) instead of di-2'-phenylethyl epoxysuccinate, 3'-phenyl-2'-propenyl potassium epoxysuccinate(EP-134) was obtained as colorless crystals from water-acetone. Yield 0.98 g (48%), m.p. 153°-155° C.

EXAMPLE 43

To a solution of 2.4 g of dimethyl epoxysuccinate in 45 ml of methanol, a solution of 0.84 g of potassium hydroxide in 8.4 ml of methanol was added with ice-cooling. The mixture was stirred for two hours and concentrated in vacuo. The residue was dissolved in 30 ml of water and acidified with concentrated sulfuric acid. The resulting solution was extracted 5 times with 30 ml of ethyl acetate. The ethyl acetate layers were combined and concentrated to dryness. Recrystallization of the residue from chloroform-hexane gave 1.31 g of methyl hydrogen epoxysuccinate(EP-135) as white plates. Yield 48%, m.p. 85°-86° C. IR$\nu_{KBr}$(cm$^{-1}$): 1760 (ester), 1715 (COOH), 900 (epoxide). NMR(CDCl$_3$)δ: 3.77 (2H, s), 3.88 (3H, s), 9.95 (1H, s).

The following compound was obtained from the corresponding material by the method as described in Example 43.

phenyl hydrogen epoxysuccinate(EP-136).

EXAMPLE 44

To a solution of 9 g of diethyl epoxysuccinate in 30 ml of ethanol, 2.7 g of potassium hydroxide in 72 ml ethanol was added with ice-cooling. The mixture was stirred for two hours, and the deposited solid was collected by filtration and washed with a small amount of ethanol. Recrystallization from aqueous ethanol gave 6.8 g of ethyl potassium epoxysuccinate(EP-137) as white prisms. Yield 72.5%. IR$\nu_{KBr}$(cm$^{-1}$): 1735 (ester), 1620 (COOK), 905 (epoxide). NMR(D$_2$O)δ: 1.3 (3H, t, J=7 Hz), 3.59 (2H, d.d., J=2 Hz), 4.29 (2H, q, J=7 Hz).

The following compounds were obtained from the corresponding materials by the method as described in Example 44.

n-propyl potassium epoxysuccinate(EP-138),
i-propyl potassium epoxysuccinate(EP-139),
allyl potassium epoxysuccinate(EP-140),
propargyl potassium epoxysuccinate(EP-141),
n-butyl potassium epoxysuccinate(EP-142),
benzyl potassium epoxysuccinate(EP-143).

EXAMPLE 45

To a solution of 8.16 g of di-n-amyl epoxysuccinate in 3 ml of n-amyl alcohol, a solution of 1.68 g of potassium hydroxide in 12 ml of amyl alcohol was added with ice-cooling. The mixture was stirred for 40 minutes and added to petroleum ether. After cooling at −10° C., the crystals thus obtained were collected and washed with petroleum ether to give 2.6 g of n-amyl potassium epoxysuccinate(EP-144). Yield 36%. IR$\nu_{Nujol}$(cm$^{-1}$): 1740 (ester), 1620 (COOK), 900 (epoxide). NMR(D$_2$O)$\delta$: 0.85 (3H, t, J=6 Hz), 1.00–2.00 (6H, m), 3.53 (2H, d.d., J=2 Hz), 4.19 (2H, t, J=6 Hz). d.d., J=2 Hz), 4.19 (2H, t, J=6 Hz).

The following compound was obtained from the corresponding material by the similar method as described in Example 45.

n-dodecyl potassium epoxysuccinate(EP-145).

EXAMPLE 46

To a solution of 1.98 g of ethyl potassium epoxysuccinate (i.e. ethyl potassium oxirane 2,3-dicarboxylate) in 50 ml of ethyl ether, a solution of 1.4 g of oxalyl chloride in 30 ml of ethyl ether was added dropwise while being stirred and cooled by ice for 30 min. After the mixture had been stirred additionally at room temperature for 2 hours, the formed precipitate was filtered. The filtrate was concentrated by evaporation under reduced pressure to give epoxysuccinic acid monoethyl ester chloride as an oil. Then, the acid chloride was dissolved in 30 ml of ethyl ether and the solution thus obtained was added dropwise to a solution of 1.6 g of L-leucine ethyl ester and 1.1 g of triethylamine dissolved in 50 ml of ethyl ether while being stirred and cooled by ice for 30 min. After the mixture had been stirred additionally at room temperature for three hours, the formed precipitate was filtered. The filtrate was evaporated under reduced pressure to give an oil. The oil thus obtained was further purified by silica gel column chromatography using chloroform-acetone (100:5) mixture as solvent to give N-(3-ethoxycarbonyloxirane-2-carbonyl)-L-leucine ethyl ester(EP-146) as a colorless oil. Yield 1.9 g (63%). Mass: m/e 301 (M+). IR$\nu_{film}$(cm$^{-1}$): 3370 (amine), 1748 (ester), 1680, 1545 (amide), 895 (epoxide). NMR(CDCl$_3$)$\delta$: 0.95 (6H, d, J=5 Hz), 1.26 (3H, t, J=7 Hz), 1.29 (3H, t, J=7 Hz), 1.64 (3H, m), 3.42 (0.5 H, d, J=2 Hz), 3.51 (0.5 H, d, J=2 Hz), 3.67 (1H, d, J=2 Hz), 4.20 (4H, q, J=2 Hz), 4.6 (1H, m), 6.35 (1H, b.).

EXAMPLE 47

When 0.65 g of epoxysuccinic acid monoallylester chloride which was prepared from 1.0 g of allyl potassium epoxysuccinate (i.e. allyl potassium oxirane 2,3-dicarboxylate) by treatment with oxalyl chloride in a manner as described in Example 46 was reacted with L-tyrosine benzyl ester in dichloromethane by the method as described in Example 46, N-(3-allyloxycarbonyloxirane-2-carbonyl)-L-tyrosine benzyl ester(EP-147) was obtained as a colorless oil. Yield 1.0 g (68%). Mass: m/e 425 (M+). IR$\nu_{film}$(cm$^{-1}$): 3480 (amine, hydroxy), 1755 (ester), 1685, 1525 (amide), 1625 (C=C), 895 (epoxide). NMR(CDCl$_3$)$\delta$: 2.98 (2H, d, J=6 Hz), 3.19 (0.5H, d, J=2 Hz), 3.43 (0.5H, d, J=2 Hz), 3.58 (0.5H, d, J=2 Hz), 3.61 (0.5H, d, J=2 Hz), 4.5–6.2 (6H, m), 5.08 (2H, d, J=3 Hz), 6.25–7.0 (4H, m), 7.25 (5H, s).

EXAMPLE 48

When epoxysuccinic acid mono m-methylbenzyl ester chloride which was prepared from m-methylbenzyl potassium epoxysuccinate (i.e. m-methylbenzyl potassium oxirane 2,3-dicarboxylate) in a manner as described in Example 46 was reacted with L-tyrosine benzyl ester in dichloromethane by the same method as described in Example 47, N-(3-m-methylbenzyloxycarbonyloxirane-2-carbonyl)-L-tyrosine benzyl ester(EP-148) was obtained as a colorless oil. Yield 61%. Mass: m/e 489 (M+). IR$\nu_{film}$(cm$^{-1}$): 3480 (amine, hydroxy), 1750 (ester, 1685, 1540 (amide), 897 (epoxide). NMR(CDCl$_3$)$\delta$: 2.30 (3H, s), 3.02 (2H, d, J=6 Hz), 3.21 (0.5H, d, J=2 Hz), 3.47 (0.5H, d, J=2 Hz), 3.60 (0.5H, d, J=2 Hz), 3.64 (0.5H, d, J=2 Hz), 4.75 (1H, m), 5.12 (4H, s), 6.35 (1H, b), 6.25–7.20 (8H, m), 7.30 (5H, s).

The following compounds were obtained from the corresponding materials by similar methods as described in Example 48.

N-(3-piperonyloxycarbonyloxirane-2-carbonyl)-L-methionene methyl ester(EP-149),
N-(3-ethoxycarbonyloxirane-2-carbonyl)-L-phenylalanine ethyl ester(EP-150),
N-(3-ethoxycarbonyloxirane-2-carbonyl)-L-tryptophan ethyl ester(EP-151),
N-(3-ethoxycarbonyloxirane-2-carbonyl)-L-proline benzyl ester(EP-152),
N-(3-n-propyloxycarbonyloxirane-2-carbonyl)-glycine benzyl ester(EP-153),
N-(3-ethoxycarbonyloxirane-2-carbonyl)-glycine benzyl ester(EP-154),
N-(3-ethoxycarbonyloxirane-2-carbonyl)-L-methionine methyl ester(EP-155),
N-(3-ethoxycarbonyloxirane-2-carbonyl)-L-glutamic acid dibenzyl ester(EP-156),
N-(3-ethoxycarbonyloxirane-2-carbonyl)-$\beta$-alanine benzyl ester(EP-157),
N-(3-ethoxycarbonyloxirane-2-carbonyl)-L-valine benzyl ester(EP-158),
N-(3-benzyloxycarbonyloxirane-2-carbonyl)-L-phenylalanine ethyl ester(EP-159),
N-(3-o-chlorobenzyloxycarbonyloxirane-2-carbonyl)-L-phenylalanine ethyl ester(EP-160),
N-(3-anisyloxycarbonyloxirane-2-carbonyl)-L-proline benzyl ester(EP-161),
N-(3-p-bromobenzyloxycarbonyloxirane-2-carbonyl)-L-valine benzyl ester(EP-162),
N$^\alpha$-(3-ethoxycarbonyloxirane-2-carbonyl)-N$^\epsilon$-carbobenzoxy-L-lysine benzyl ester(EP-163),
N$^\alpha$-(3-allyloxycarbonyloxirane-2-carbonyl)-N$^\epsilon$-carbobenzoxy-L-lysine benzyl ester(EP-164),
N$^\alpha$-(3-propargyloxycarbonyloxirane-2-carbonyl)-N$^\epsilon$-carbobenzoxy-L-lysine benzyl ester(EP-165),
N-(3-methoxycarbonyloxirane-2-carbonyl)-L-leucine ethyl ester(EP-166),
N-(3-ethoxycarbonyloxirane-2-carbonyl)-L-leucine amide (EP-167),
N-(3-ethoxycarbonyloxirane-2-carbonyl)-L-glutamine benzyl ester(EP-168),
N$^\alpha$-(3-ethoxycarbonyloxirane-2-carbonyl)-N$^\epsilon$-p-methoxybenzyloxycarbonyl-L-lysine benzyl ester-(EP-169), N$^\alpha$-(3-ethoxycarbonyloxirane-2-carbonyl)-N$^\epsilon$-t-butyloxycarbonyl-L-lysine benzyl ester(EP-170), N$^\alpha$-(3-benzyloxycarbonyloxirane-2-carbonyl)-N$^\epsilon$-formyl-L-lysine benzyl ester(EP-171), N$^\alpha$-(3-ethoxycarbonyloxirane-2-carbonyl)-N$^\delta$-acetyl-L-ornithine benzyl ester(EP-172), N$^\alpha$-(3-ethoxycarbonyloxirane-2-carbonyl)-N$^\delta$-benzoyl-L-ornithine benzyl ester(EP-173).

EXAMPLE 49

To a solution of 0.5 g of N-(3-ethoxycarbonyloxirane-2-carbonyl)-L-leucine ethyl ester(EP-146) dissolved in 2 ml of ethanol and 1 ml of water, a solution of 0.3 g of potassium hydroxide dissolved in 1 ml of water was added. After the mixture had been stirred at room temperature for 2 hours, 40 ml of ethanol was added to the mixture. The formed precipitate was filtered and recrystallized from ethanol-water to give N-(3-carboxyoxirane-2-carbonyl)-L-leucine dipotassium salt(EP-174) as colorless needles. Yield 0.32 g (60%), m.p. 210° C.

The following compounds were obtained by a method as described in Example 49.

N-(3-carboxyoxirane-2-carbonyl)-L-phenylalanine dipotassium salt(EP-175),

N-(3-carboxyoxirane-2-carbonyl)-N-carbobenzoxy-L-lysine dipotassium salt(EP-176).

EXAMPLE 50

After saponification of 0.15 g of N-(ethoxycarbonyloxirane-2-carbonyl)-L-tryptophan ethyl ester with potassium hydroxide in an analogous experiment of Example 49, the reaction mixture was acidified with hydrochloric acid and extracted with ethyl ether. Evapolation of the solvent gave N-(3-carboxyoxirane-2-carbonyl)-L-tryptophan(EP-177) as colorless powders. Yield 0.1 g (87%), m.p. 113° C.

EXAMPLE 51

To a solution of 5.1 g of N$^G$-nitro-L-arginine benzyl ester ditosylate, 1.7 g of benzyl hydrogen epoxysuccinate (i.e. benzyl hydrogen oxirane 2,3-trans dicarboxylate), 1.6 g of methyl morpholine and 1.3 g of N-hydroxysuccinimide dissolved in 30 ml of dimethylformamide, a solution of 3.0 g of dicyclohexylcarbodiimide dissolved in 20 ml of dimethylformamide was added dropwise with stirring at −10° C. The mixture was stirred for one hour at −10° C. and for another one hour at room temperature and was allowed to stand overnight. After filtration of the precipitate thus formed, the filtrate was diluted with 200 ml of ethyl acetate and washed with saturated sodium bicarbonate solution and saturated sodium chloride, in turn. The organic layer was dried over magnesium sulfate and evaporated to dryness. Silica gel column chromatography using chloroformmethanol (25:1) as solvent and recrystallization from acetone-n-hexane provided N-(3-benzyloxycarbonyloxirane-2-carbonyl)-N$^G$-nitro-L-arginine benzyl ester(EP-178) as colorless needles. Yield 2.4 g (61%), m.p. 141°–142° C.

The following compounds were obtained by a method as described in Example 51.

N$^\alpha$-(phenoxycarbonyloxirane-2-carbonyl)-N$^\epsilon$-carbobenzoxy-L-lysine benzyl ester(EP-179), N$^\alpha$-(3-iso-propyloxycarbonyloxirane-2-carbonyl)-N$^\epsilon$-carbobenzoxy-L-lysine benzyl ester(EP-180), N$^\alpha$-(3-p-methylbenzyloxycarbonyloxirane-2-carbonyl)-N$^\epsilon$-carbobenzoxy-L-lysine benzyl ester(EP-181), N$^\alpha$-(3-benzyloxycarbonyloxirane-2-carbonyl)-N$^\delta$-carbobenzoxy-L-ornithine benzyl ester(EP-182), N$^\alpha$-(3-n-buthoxycarbonyloxirane-2-carbonyl)-N$^\delta$-carbobenzoxy-L-ornithine benzyl ester(EP-183), N$^\alpha$-(3-benzyloxycarbonyloxirane-2-carbonyl)-N$^G$-nitro-L-arginine methyl ester(EP-184), N$^\alpha$-(3-ethoxycarbonyloxirane-2-carbonyl)-L-histidine methyl ester(EP-185), N$^\alpha$-(3-ethoxycarbonyloxirane-2-carbonyl)-L-serine ethyl ester(EP-186), N$^\alpha$-(3-phenethyloxycarbonyloxirane-2-carbonyl)-N$^\epsilon$-carbobenzoxy-L-lysine benzyl ester(EP-187), N$^\alpha$-[3-(3'-phenylpropyloxy)-carbonyloxirane-2-carbonyl]-N$^\epsilon$-carbobenzoxy-L-lysine benzyl ester(EP-188), N-(3-p-chlorobenzyloxycarbonyloxirane-2-carbonyl)-γ-aminobutylic acid ethyl ester(EP-189), N-(3-methoxycarbonyloxirane-2-carbonyl)-L-threonine ethyl ester(EP-190), N-(3-benzyloxycarbonyloxirane-2-carbonyl)-S-benzyl-L-cysteine benzyl ester(EP-191), N-(3-ethoxycarbonyloxirane-2-carbonyl)-L-alanine-t-butyl ester(EP-192), N-(3-ethoxycarbonyloxirane-2-carbonyl)-L-aspartic acid dibenzyl ester(EP-193), N-(3-ethoxycarbonyloxirane-2-carbonyl)-L-asparagine benzyl ester(EP-194).

EXAMPLE 52

To a solution of 0.512 g of N$^\alpha$-(3-ethoxycarbonyloxirane-2-carbonyl)-N$^\epsilon$-carbobenzoxy-L-lysine ethyl ester in 10 ml of ethanol, a solution of 0.056 g of potassium hydroxide in 5 ml of ethanol was added dropwise under ice cooling. The precipitate thus formed was filtered and reprecipitated from water-ethanol to give N$^\alpha$-(3-carboxyoxirane-2-carbonyl)-N$^\epsilon$-carbobenzoxy-L-lysine ethyl ester potassium salt(EP-195) as a colorless powder. Yield 0.32 g (75%), m.p. 148°–149° C.

The following compounds were obtained from the corresponding materials by a method as described in Example 51.

N$^\alpha$-(3-carboxyoxiane-2-carbonyl)-N$^\delta$-carbobenzoxy-L-ornithine benzyl ester potassium salt(EP-196), N$^\alpha$-(3-carboxyoxirane-2-carbonyl)-N$^\epsilon$-carbobenzoxy-L-lysine benzyl ester potassium salt(EP-197), N$^\alpha$-(3-carboxyoxirane-2-carbonyl)-N$^\delta$-carbobenzoxy-L-ornithine methyl ester potassium salt(EP-198), N$^\alpha$-(3-carboxyoxirane-2-carbonyl)-N$^\delta$-carbobenzoxy-L-ornithine n-butyl ester potassium salt(EP-199),

EXAMPLE 53

A mixture of 0.4 g of N-(3-benzyloxycarbonyloxirane-2-carbonyl)-N$^G$-nitro-L-arginine methyl ester(EP-184) dissolved in 25 ml of the methanol-acetic acid-water (8/2/1=v/v/v) mixture was stirred in the presence of 0.1 g of 5% palladium carbon under stream of H$_2$ at room temperature for 4 hours. After removal of catalyst by filtration, the filtrate was evaporated under reduced pressure to give an oil. This was dissolved in water and extracted with ethyl acetate. The aqueous layer was evaporated under reduced pressure to give a solid. Further purification of this by Sephadex LH-20 column chromatography (Farmacia Co.) using 5% aqueous methanol solution as solvent afforded N-(3-carboxyoxirane-2-carbonyl)-L-arginine methyl ester(EP-200) as colorless glassy crystals. Yield 0.21 g (76%), m.p. 99°–102° C.

The following compounds were obtained from the corresponding materials by a method as described in Example 53.

N-(3-ethoxycarbonyloxirane-2-carbonyl)-L-lysine(EP-201),

N-(3-carboxyoxirane-2-carbonyl)-L-arginine(EP-202).

EXAMPLE 54

By substituting one g of L-leucine ethyl ester hydrochloride and 1.2 g of 3'-cyclopentyl-propyl hydrogen epoxysuccinate for $N^G$-nitro-L-arginine benzyl ester ditosylate and benzyl hydrogen epoxysuccinate in Example 51, N-[3-(3'-cyclopentylpropyloxy)carbonyloxirane-2-carbonyl]-L-leucine ethyl ester(EP-203) was obtained as an oil. Yield 1.2 g (62%). Mass: m/e 383 (M+). IR$\nu_{film}$(cm$^{-1}$): 3370 (amine), 1750 (ester), 1680, 1545 (amide), 895 (epoxide). NMR(CDCl$_3$)δ: 0.95 (6H, d, J=5 Hz), 1.30 (3H, t, J=7 Hz), 0.8–2.1 (16H, m), 3.42 (0.5H, d, J=2 Hz), 3.53 (0.5H, d, J=2 Hz), 3.67 (1H, d, J=2 Hz), 4.05 (2H, t, J=7 Hz), 4.13 (2H, q, J=7 Hz), 4.2–4.8 (1H, m), 6.0–6.7 (1H, b.).

The following compounds were obtained from the corresponding material by a method as described in Example 54.

$N^\alpha$-(3-cyclopropyloxycarbonyloxirane-2-carbonyl)-$N^\epsilon$-carbobenzoxy-L-lysine benzyl ester(EP-204), N-(3-cyclopentyloxycarbonyloxirane-2-carbonyl)-L-valine benzyl ester(EP-205), N-[3-(1'-cyclopentylethoxy)-carbonyloxirane-2-carbonyl]-L-lysine benzyl ester(EP-206), N-[3-(2'-cyclohexylethoxy)-carbonyloxirane-2-carbonyl]-glycine benzyl ester(EP-207), N-[3-(4'-cyclohexylbutoxy)-carbonyloxirane-2-carbonyl]-β-alanine benzyl ester(EP-208), N-(3-cyclooctyloxycarbonyloxirane-2-carbonyl)-L-glutamic acid dibenzyl ester(EP-209), N-[3-(2'-adanatyloxy)-carbonyloxirane-2-carbonyl]-L-phenyl alanine ethyl ester(EP-210), N-[3-(3'-cyclohexen-1-yl)-methoxycarbonyloxirane-2-carbonyl]-L-tyrosine benzyl ester(EP-211).

EXAMPLE 55

By substituting 1.14 g of 2-cis-methylcyclohexyl hydrogen epoxysuccinate and 1.2 g of L-phenylalanine ethyl ester hydrochloride for benzyl hydrogen epoxysuccinate and $N^G$-nitro-L-arginine benzyl ester ditosylate in Example 51, N-[3-(2'-cis-methylcyclohexyloxy)-carbonyloxirane-2-carbonyl]-L-phenylalanine ethyl ester(EP-212) was obtained as an oil. Yield 1.1 g (54.6%). Mass: m/e 403 (M+). IR$\nu_{film}$(cm$^{-1}$): 3400 (amine), 1753 (ester), 1680, 1540 (amide), 897 (epoxide). NMR(CDCl$_3$)δ: 0.88 (3H, d, J=7 Hz), 1.20 (1.5H, t, J=7 Hz), 1.22 (1.5H, t, J=7 Hz), 1.45 (8H, b, s.), 3.06 (2H, d, J=6 Hz), 3.15 (0.5H, d, J=2 Hz), 3.47 (0.5H, d, J=2 Hz), 3.58 (0.5H, d, J=2 Hz), 3.62 (0.5H, d, J=2 Hz), 4.0 (1H, q, J=7 Hz), 4.15 (1H, q, J=7 Hz), 4.5–5.0 (1H, m), 5.02 (1H, b.s.), 5.12 (1H, s), 6.2–6.5 (1H, b.s.), 6.8–7.4 (5H, m).

The following compounds were obtained from the corresponding material by a method as described in Example 55.

N-[3-(2'-cis-chlorocyclopentyloxy)-carbonyloxirane-2-carbonyl]-glycine benzyl ester(EP-213), N-[3-(2'-trans-bromocyclopentyloxy)-carbonyloxirane-2-carbonyl]-L-leucine benzyl ester(EP-214), N-[3-(4'-trans-methylcyclohexyloxy)-carbonyloxirane-2-carbonyl]-L-alanine methyl ester(EP-215).

EXAMPLE 56

By substituting 1.14 g of thenyl hydrogen epoxysuccinate and 2.7 g of L-glutamic acid dibenzyl ester tosylate for benzyl hydrogen epoxysuccinate and $N^G$-nitro-L-arginine benzyl ester ditosylate in Example 51, N-(3-thenyloxycarbonyloxirane-2-carbonyl)-L-glutamic acid dibenzyl ester(EP-216) was obtained as an oil. Yield 1.5 g (55.9%). Mass: m/e 537 (M+). IR$\nu_{film}$(cm$^{-1}$): 3400 (amine), 1755 (ester), 1690, 1540 (amide), 895 (epoxide). NMR(CDCl$_3$)δ: 2.0–2.6 (4H, m), 3.45 (1H, d, J=2 Hz), 3.62 (1H, d, J=2 Hz), 4.4–4.8 (1H, m), 5.05 (2H, s), 5.10 (2H, d, J=2 Hz), 5.42 (2H, s), 6.5–6.9 (1H, b.), 6.9–7.9 (3H, m), 7.29 (10H, s).

The following compounds were obtained from the corresponding materials by a method as described in Example 56.

N-[3-furfuryloxycarbonyloxirane-2-carbonyl]-L-leucine n-butyl ester(EP-217),

N-[3-tetrahydrofurfuryloxycarbonyloxirane-2-carbonyl]-L-phenylalanine t-butyl ester(EP-218), N-[3-(1'-naphthylmethoxycarbonyloxirane-2-carbonyl]-L-valine ethyl ester(EP-219), N-[3-(5'-bromo-2-naphthylmethoxy)-carbonyloxirane-2-carbonyl]-glycine ethyl ester(EP-220).

What is claimed is:

1. Trans-epoxysuccinic acid derivatives represented by the general formula

wherein
(1) R$^1$ and R$^2$ are each R$^3$ wherein R$^3$ is —O—A$^1$—R$^4$, —O—A$^2$—R$^5$ or —OCH$_2$—R$^6$ wherein A$^1$ is alkylene containing zero to 4 carbon atoms or said alkylene substituted with methyl, R$^4$ is cycloalkyl containing 3 to 10 carbon atoms, or said cycloalkyl substituted with one to 3 halogen or methyl, A$^2$ is alkylene containing 2 or 3 carbon atoms, or alkenylene containing 2 or 3 carbon atoms, R$^5$ is phenyl, R$^6$ is furyl, tetrahydrofuryl, thienyl, naphthyl, naphthyl substituted with one or two halogen or methyl, phenyl substituted with one to three halogen, methyl, methoxy, methylenedioxy or trifluoromethyl, or cycloalkenyl containing 5 to 8 carbon atoms, or
(2) R$^1$ is hydroxy, R$^3$ or R$^7$, and R$^2$ is hydroxy or R$^8$ wherein R$^3$ is as defined above, R$^7$ is alkoxy containing one to 12 carbon atoms, allyloxy, propargyloxy, phenoxy or benzyloxy, and R$^8$ is an amino acid residue represented by the general formula

—NH—A$^3$—COR$^9$ wherein A$^3$ is methylene, ethylene, trimethylene, alkylidene containing 2 to 5 carbon atoms or said alkylidene substituted with one to 3 hydroxy, methyl, thiol, methylthio, benzylthio, phenyl, phenyl substituted with hydroxy or halogen, indazolyl, imidazolyl,—$COR^{10}$ or —$NHR^{11}$ wherein $R^{10}$ is amino or —$OR^{12}$ wherein $R^{12}$ is hydrogen, alkyl containing one to 5 carbon atoms, benzyl or an alkali metal cation, and $R^{11}$ is hydrogen, formyl, alkoxycarbonyl containing 2 to 5 carbon atoms, benzyloxycarbonyl, methoxybenzyloxycarbonyl, tosyl, guanyl, or guanyl substituted by nitro, and $R^9$ is amino or —$OR^{13}$ wherein $R^{13}$ is hydrogen, alkyl containing one to 5 carbon atoms, benzyl or an alkali metal cation, with the proviso that $R^1$ is neither hydroxy, alkoxy containing one to 12 carbon atoms, nor phenoxy when $R^2$ is hydroxy, and salts thereof when $R^1$ or $R^2$ is hydroxy.

2. A compound according to claim 1 wherein $R^1$ and $R^2$ are each —O—$A^1$—$R^4$ wherein $A^1$ is alkylene containing zero to 4 carbon atoms or said alkylene substituted with methyl, and $R^4$ is cycloalkyl containing 3 to 10 carbon atoms, or said cycloalkyl substituted with one to 3 halogen or methyl.

3. A compound according to claim 1 wherein $R^1$ and $R^2$ are each —O—$A^2$—$R^5$ wherein $A^2$ is alkylene containing 2 or 3 carbon atoms or alkenylene containing 2 or 3 carbon atoms, and $R^5$ is phenyl.

4. A compound according to claim 1 wherein $R^1$ and $R^2$ are each —$OCH_2$—$R^6$ wherein $R^6$ is furyl, tetrahydrofuryl, thienyl, naphthyl, naphthyl substituted with one or two halogen or methyl, phenyl substituted with one to three halogen, methyl, methoxy, methylenedioxy or trifluoromethyl, or cycloalkenyl containing 5 to 8 carbon atoms.

5. A compound according to claim 1 wherein $R^1$ is —O—$A^1$—$R^4$ and $R^2$ is hydroxy wherein $A^1$ is alkylene containing zero to 4 carbon atoms or said alkylene substituted with methyl, and $R^4$ is cycloalkyl containing 3 to 10 carbon atoms, or said cycloalkyl substituted with one to 3 halogen or methyl.

6. A compound according to claim 1 wherein $R^1$ is —O—$A^2$—$R^5$ and $R^2$ is hydroxy wherein $A^2$ is alkylene containing 2 or 3 carbon atoms or alkenylene containing 2 or 3 carbon atoms, and $R^5$ is phenyl.

7. A compound according to claim 1 wherein $R^1$ is —$OCH_2$—$R^6$ and $R^2$ is hydroxy wherein —$R^6$ is furyl, tetrahydrofuryl, thienyl, naphthyl, naphthyl substituted with one or two halogen or methyl, phenyl substituted with one to three halogen, methyl, methoxy, methylenedioxy or trifluoromethyl, or cycloalkenyl containing 5 to 8 carbon atoms.

8. A compound according to claim 1 wherein $R^1$ is allyloxy, propargyloxy or benzyloxy and $R^2$ is hydroxy.

9. A compound according to claim 1 wherein $R^1$ is —O—$A^1$—$R^4$ and $R^2$ is $R^8$ wherein $A^1$ is alkylene containing zero to 4 carbon atoms or said alkylene substituted with methyl, $R^4$ is cycloalkyl containing 3 to 10 carbon atoms, or said cycloalkyl substituted with one to 3 halogen or methyl, and $R^8$ is an amino acid residue represented by the general formula

—NH—$A^3$—$COR^9$ wherein $A^3$ is methylene, ethylene, trimethylene, alkylidene containing 2 to 5 carbon atoms or said alkylidene substituted with one to 3 hydroxy, methyl, thiol, methylthio, benzylthio, phenyl, phenyl substituted with hydroxy or halogen, indazolyl, imidazolyl, —$COR^{10}$ or —$NHR^{11}$ wherein $R^{10}$ is amino or —$OR^{12}$ wherein $R^{12}$ is hydrogen, alkyl containing one to 5 carbon atoms, benzyl or an alkali metal cation, and $R^{11}$ is hydrogen, formyl, alkoxycarbonyl containing 2 to 5 carbon atoms, benzyloxycarbonyl, methoxybenzyloxycarbonyl, tosyl, guanyl, or guanyl substituted by nitro, and $R^9$ is amino or —$OR^{13}$ wherein $R^{13}$ is hydrogen, alkyl containing one to 5 carbon atoms, benzyl or an alkali metal cation.

10. A compound according to claim 1 wherein $R^1$ is —O—$A^2$—$R^5$ and $R^2$ is $R^8$ wherein $A^2$ is alkylene containing 2 or 3 carbon atoms or alkenylene containing 2 or 3 carbon atoms, $R^5$ is phenyl, and $R^8$ is an amino acid residue represented by the general formula

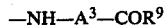
—NH—$A^3$—$COR^9$ wherein $A^3$ is methylene, ethylene, trimethylene, alkylidene containing 2 to 5 carbon atoms or said alkylidene substituted with one to 3 hydroxy, methyl, thiol, methylthio, benzylthio, phenyl, phenyl substituted with hydroxy or halogen, indazolyl, imidazolyl, —$COR^{10}$ or —$NHR^{11}$ wherein $R^{10}$ is amino or —$OR^{12}$ wherein $R^{12}$ is hydrogen, alkyl containing one to 5 carbon atoms, benzyl or alkali metal cation, and $R^{11}$ is hydrogen, formyl, alkoxycarbonyl containing 2 to 5 carbon atoms, benzyloxycarbonyl, methoxybenzyloxycarbonyl, tosyl, guanyl, or guanyl substituted by nitro, and $R^9$ is amino or —$OR^{13}$ wherein $R^{13}$ is hydrogen, alkyl containing one to 5 carbon atoms, benzyl or an alkali metal cation.

11. A compound according to claim 1 wherein $R^1$ is —$OCH_2$—$R^6$ and $R^2$ is $R^8$ wherein $R^6$ is furyl, tetrahydrofuryl, thienyl, naphthyl, naphthyl substituted with one or two halogen or methyl, phenyl substituted with one to three halogen, methyl, methoxy, methylenedioxy or trifluoromethyl, or cycloalkenyl containing 5 to 8 carbon atoms and $R^8$ is an amino acid residue represented by the general formula

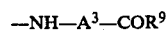
—NH—$A^3$—$COR^9$ wherein $A^3$ is methylene, ethylene, trimethylene, alkylidene containing 2 to 5 carbon atoms or said alkylidene substituted with one to 3 hydroxy, methyl, thiol, methylthio, benzylthio, phenyl, phenyl substituted with hydroxy or halogen, indazolyl, imidazolyl, —$COR^{10}$ or —$NHR^{11}$ wherein $R^{10}$ is amino or —$OR^{12}$ wherein $R^{12}$ is hydrogen, alkyl containing one to 5 carbon atoms, benzyl or an alkali metal cation, and $R^{11}$ is hydrogen, formyl, alkoxycarbonyl containing 2 to 5 carbon atoms, benzyloxycarbonyl, methoxybenzyloxycarbonyl, tosyl, guanyl, or guanyl substituted by nitro, and $R^9$ is amino or —$OR^{13}$ wherein $R^{13}$ is hydrogen, alkyl containing one to 5 carbon atoms, benzyl or an alkali metal cation.

12. A compound according to claim 1 wherein $R^1$ is $R^7$ and $R^2$ is $R^8$ wherein $R^7$ is alkoxy containing one to 12 carbon atoms, allyloxy, propargyloxy, phenoxy or benzyloxy, and $R^8$ is an amino acid residue represented by the general formula

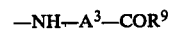
—NH—$A^3$—$COR^9$ wherein $A^3$ is methylene, ethylene, trimethylene, alkylidene containing 2 to 5 carbon atoms or said alkylidene substituted with one to 3 hydroxy, methyl, thiol, methylthio, benzylthio, phenyl, phenyl substituted with hydroxy or halogen, indazolyl, imidazolyl, —$COR^{10}$ or —$NHR^{11}$ wherein $R^{10}$ is amino or —$OR^{12}$ wherein $R^{12}$ is hydrogen, alkyl containing one to 5 carbon atoms, benzyl or alkali metal cation, and $R^{11}$ is hydrogen, formyl, alkoxycarbonyl containing 2 to 5 carbon atoms, benzyloxycarbonyl, methoxybenzyloxycarbonyl, tosyl, guanyl, or guanyl substituted by nitro, and $R^9$ is amino or —$OR^{13}$ wherein $R^{13}$ is hydrogen, alkyl containing one to 5 carbon atoms, benzyl or an alkali metal cation.

13. A compound according to claim 1 wherein $R^1$ is hydroxy and $R^2$ is $R^8$ wherein $R^8$ is an amino acid residue represented by the general formula $$-NH-A^3-COR^9$$

wherein $A^3$ is methylene, ethylene, trimethylene, alkylidene containing 2 to 5 carbon atoms or said alkylidene substituted with one to 3 hydroxy, methyl, thiol, methylthio, benzylthio, phenyl, phenyl substituted with hydroxy or halogen, indazolyl, imidazolyl, $-COR^{10}$ or $-NHR^{11}$ wherein $R^{10}$ is amino or $-OR^{12}$ wherein $R^{12}$ is hydrogen, alkyl containing one to 5 carbon atoms, benzyl or alkali metal cation, and $R^{11}$ is hydrogen, formyl, alkoxycarbonyl containing 2 to 5 carbon atoms, benzyloxycarbonyl, methoxybenzyloxycarbonyl, tosyl, guanyl, or guanyl substituted by nitro, and $R^9$ is amino or $-OR^{13}$ wherein $R^{13}$ is hydrogen, alkyl containing one to 5 carbon atoms, benzyl or an alkali metal cation.

14. Trans-epoxysuccinic acid derivatives represented by the general formula

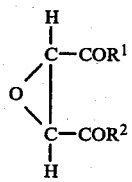

wherein
(1) $R^1$ and $R^2$ are each $R^3$ wherein $R^3$ is $-O-A^1-R^4$, $-O-A^2-R^5$ or $-OCH_2-R^6$ wherein $A^1$ is alkylene containing zero to 4 carbon atoms or said alkylene substituted with methyl, $R^4$ is cycloalkyl containing 3 to 10 carbon atoms, or said cycloalkyl substituted with one to 3 halogen or methyl, $A^2$ is alkylene containing 2 or 3 carbon atoms, or alkenylene containing 2 or 3 carbon atoms, $R^5$ is phenyl, $R^6$ is furyl, tetrahydrofuryl, thienyl, naphthyl, naphthyl substituted with one or two halogen or methyl, or phenyl substituted with one to three halogen, methyl, methoxy, methylenedioxy or trifluoromethyl, or cycloalkenyl containing 5 to 8 carbon atoms, or (2) $R^1$ is hydroxy or $R^3$ and $R^2$ is hydroxy or $R^8$ wherein $R^3$ is as defined above, and $R^8$ is an amino acid residue represented by the formula $$-NH-A^3-COR^9$$

wherein $A^3$ is methylene, ethylene, trimethylene, alkylidene containing 2 to 5 carbon atoms or said alkylidene substituted with one to 3 hydroxy, methyl, thiol, methylthio, benzylthio, phenyl, phenyl substituted with hydroxy or halogen, indazolyl, imidazolyl, $-COR^{10}$ or $-NHR^{11}$ wherein $R^{10}$ is amino or $-OR^{12}$ wherein $R^{12}$ is hydrogen, alkyl containing one to 5 carbon atoms, benzyl or an alkali metal cation, and $R^{11}$ is hydrogen, formyl, alkoxycarbonyl containing 2 to 5 carbon atoms, benzyloxycarbonyl, methoxybenzyloxycarbonyl, tosyl, guanyl, or guanyl substituted by nitro, and $R^9$ is amino or $-OR^{13}$ wherein $R^{13}$ is hydrogen, alkyl containing one to 5 carbon atoms, benzyl or an alkali metal cation, with the proviso that $R^1$ is not hydroxy when $R^2$ is hydroxy, and salts thereof when $R^1$ or $R^2$ is hydroxy.

* * * * *